US006455042B1

(12) United States Patent
Brenner et al.

(10) Patent No.: US 6,455,042 B1
(45) Date of Patent: Sep. 24, 2002

(54) METHOD OF TREATING ULCERATIVE COLITIS OR CROHN'S DISEASE BY ADMINISTERING AN ANTIBODY TO $\alpha^E\beta^7$ INTEGRIN

(75) Inventors: Michael B. Brenner, Sherborn; Christina M. Parker, Arlington, both of MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 09/293,238

(22) Filed: Apr. 16, 1999

Related U.S. Application Data

(62) Division of application No. 08/879,338, filed on Jun. 20, 1997, now Pat. No. 6,063,906, which is a division of application No. 08/663,731, filed on Jun. 14, 1996, now Pat. No. 6,057,423, which is a division of application No. 08/199,776, filed on Feb. 18, 1994, now Pat. No. 5,594,120.

(51) Int. Cl.$^7$ .............................................. A61K 39/395
(52) U.S. Cl. ................ 424/144.1; 424/130.1; 424/139.1; 424/141.1; 424/143.1; 424/152.1; 424/153.1; 424/154.1
(58) Field of Search ........................... 424/130.1, 139.1, 424/172.1, 141.1, 143.1, 144.1, 152.1, 153.1, 154.1; 514/12, 885, 2, 8; 530/387.1, 387.9, 388.22, 388.7, 388.73, 388.75

(56) References Cited

U.S. PATENT DOCUMENTS

| | | |
|---|---|---|
| 3,652,761 A | 3/1972 | Weetal |
| 4,478,946 A | 10/1984 | Van der Merwe et al. |
| 4,554,088 A | 11/1985 | Whitehead et al. |
| 5,002,873 A | 3/1991 | St. John et al. |
| 5,120,830 A | 6/1992 | Santoro |
| 5,188,959 A | 2/1993 | Haberman |
| 5,206,345 A | 4/1993 | Masinovsky et al. |
| 5,211,657 A | 5/1993 | Yamada et al. |
| 5,432,018 A | 7/1995 | Dower et al. |
| 5,594,120 A | 1/1997 | Brenner et al. |
| 5,610,281 A | 3/1997 | Brenner et al. |

FOREIGN PATENT DOCUMENTS

| | | |
|---|---|---|
| WO | WO-95/29693 | 11/1953 |
| WO | WO-91/07977 | 6/1991 |
| WO | WO-94/11401 | 5/1994 |
| WO | WO-95/22610 | 8/1995 |

OTHER PUBLICATIONS

Cornejo et al., Advances in Pharmacology, vol. 39, 1997.*
Ward et al., Therapeutic Immunology, 1:165–171, 1994.*
Higgins et al., J. of Biological Chemistry, 275(33):25652–25664, Aug. 2000.*
Ludviksson et al., J. of Immunology, 162:4975–4982, 1999.*
T. Ferguson et al., Two integrin–binding peptides abrogate T cell–mediated immune response in vivo, Proc. Natl. Acad. Sci. USA, vol. 88: 8072–8076, Sep. 1991.
D. Taylor et al., A Peptide Corresponding to GPIIb$\alpha$ 300–312, a Presumptive Fibrinogen $\lambda$–Chain Binding Site on the Platelet Integrin GPIIb/IIIa, Inhibits the Adhesion of Platelets to at Least Four Adhesive Ligands, J. Bio Chem.; Jun. 15, 1992: 267, 11729–11733.
N. Vedder et al., Inhibition of leukocyte adherence by anti–CD18 monoclonal antibody attenuates Reperfusion injury in the rabbit ear, Proc. Natl. Acad. Sci. USA, vol. 87: 2643–2646, Apr. 1990.
T. Yednock et al., Prevention of experimental autoimmune encephalomyelitis by antibodies against $\alpha 4\beta 1$ integrin, Nature, 356, Mar. 5, 1992:63–66.
Cepek, K.L. et al., Integrin $\alpha^E\beta_7$ Mediates Adhesion of T Lymphocytes to Epithelial Cells, J. Immunol., 150: 3459–3470 (1993).
Parker, C.M. et al., A family of $\beta_7$ integrins on human mucosal lymphocytes, Proc. Natl. Acad. Sci. USA 89: 1924–1928 (1992).
Hochstenbach, F. et al., Characterization of a Third Form of the Human T Cell Receptor, J. Exp. Med. 168:761–776 (1988).
Moller, P. et al., Rapid Communication–Monoclonal Antibody HML–1, a marker for Intraepithelial T Cells and Lymphomas Derived Thereof, Also Recognizes Hairy Cell Leukemia and Some B–cell Lymphomas, Amer. Amer. J. Path. 136: 509–512 (1990).
Visser, L. et al., Monoclonal Antibodies Reactive with Hairy Cell Leukemia, Blood 74: 320–325 (1989).
Cerf–Bensussan, N. et al., A monoclonal antibody (HML–1) defining a novel membrane molecule present on human intestinal lymphocytes, Eur. J. Immunol. 17: 1279–1285 (1987).
Kruschwitz, M. et al., Ber–ACT8: New monoclonal antibody to the mucosa lymphocyte antigen, J. Clin. Path 44, 636–645 Path 44, 636–645 (1991).
Pallesen, G. et al., Specificity of monoclonal antibody HML–1, Lancet 335: 537 (1990).
Visser, L. et al., Induction of B–cell chronic lymphocytic leukaemia and hairy cell leukaemia like phenotypes by by phorbol ester treatment of normal peripheral blood B–cells, Brit. J. Haematol. 75: 359–365 (1990).
T. Springer, Adhesion receptors of the immune system, Nature, 346: 425–434 (1990).

(List continued on next page.)

Primary Examiner—Phillip Gambel
Assistant Examiner—Jessica H. Roark
(74) Attorney, Agent, or Firm—Wolf, Greenfield & Sacks, P.C.

(57) ABSTRACT

The present invention relates to a method for treating an autoimmune disease, such ulcerative coliteis or crohns disease characterized by lymphocyte accumulation at epithelial sites. The method involves administering to a subject an effective amount of an antibody that selectively binds to an $\alpha^E\beta_7$ integrin or an $\alpha^E$ subunit thereof.

4 Claims, 6 Drawing Sheets-

OTHER PUBLICATIONS

S. Albelda, Biology of Disease—Role of Integrins and Other Cell Adhesion Molecules in Tumor Progression and Metastasis, Laboratory Investigation, 68: 4–17 (1993).

Cerf–Bensussan, N. et al., The human intraepithelial lymphocyte marker HML–1 is an integrin consisting of a a $\beta 7$ subunit associated with a distinctive $\alpha$ chain, Eur. J. Immunol., 22,:273–277 (1992).

Krissansen, G.W. et al., Immunologic and structural relatedness of the integrin $\beta_7$ complex and the human intraepithelial lymphocyte antigen HML–1, FEBS Letts. 296: 25–28 (1992).

A. Leff et al., Inflammation and cell–cell interactions in airway hyperresponsiveness, Am. Physiological Soc. Soc., 189–206 (1991).

R. Seth et al., ICAM–2 peptides mediate lymphocyte adhesion by binding to CDIIa/CD18 and CD49d/CD29 integrins, FEBS Letters 282: 193–196 (1991).

M. Conrad et al., A concise Review: Iron Absorption–The Mucin–Mobilferrin–Integrin Pathway. A Competitive Pathway for Metal Absorption, Am. J. Hematology, 42: 42–67 (1993).

S. Mette et al., Distribution of Integrin Cell Adhesion Receptors on Normal Bronchial Epithelial Cells and Lung Cancer Cells In Vitro and In Vivo, Am. J. Respir. Cell Mol. Biol., 8: 562–572 (1993).

E. Uhlmann et al.,Antisense Oligonucleotides: A New Therapeutic Principle Chemical Reviews, vol. 90(4): 543–584 (1990).

J. Holt et al., An Oligomer Complementary to c–myc MRNA Inhibits Proliferation of HL–60 Promyelocytic Cells and Induces Differentiation, Mol. Cell Biol., 8(2): 963–973 (1988).

M. Cooney et al., Site–Specific Oligonucleotide Binding Represses Transcription of the Human c–myc Gene, In Vitro, Science, vol. 241: 456–459 (1988).

C. Hélène et al., Oligodeoxynucleotides covalently linked to intercalating agents: a new class of gene regulatory substances, Biochimie, 67: 777–783 (1985).

W. James, Towards gene–inhibition therapy: a review of progress and prospects in the field of antiviral antisense nucleic acids and ribozymes, Antiviral Chem. & Chemo. 2(4): 191–214 (1991).

R. Weiss, Upping the Antisense Ante–Scientists bet on profits from reverse genetics, Science News, 139: 108–109 (1991).

M. Arnaout et al., Molecular cloning of the $\alpha$ subunit of human and guinea pig leukocyte adhesion glycoprotein Mol: Chromosomal localization and homology to the $\alpha$ subunits of integrins, Proc. Natl. Acad. Sci. USA, 85: 2776–2780 (1988).

T. Lallier et al., Inhibition of Neural Crest Cell Attachment by Integrin Antisense Oligonucleotides, Science, 259: 692–695 (1993).

A. Shatzman et al., Expression, Identification, and Characterization of Recombinant Gene Products in *Escherichia coli*, Methods in Enzymology, 152: 661–673 (1986).

Roberts, K. et al., The Mucosal T Cell Integrin Alpha –M–290–Beta–7 Recognizes a Ligand on Mucosal Epithelial Cell Lines, Eur J. Immunol. 23 (7): 1630–1635 (1993).

Shaw, S. et al., Molecular Cloning of the Human Mucosal Lymphocyte Intergrin Alpha–E Subunit: Unusual Structure and Restricted RNA Distribution, Journal of Biological Chemistry, 269(8): 6016–6025 (1994).

Tidd, D., A Potential Role for Antisense Oligonucleotide Analogues in the Development of Oncogene Targeted Cancer Chemotherapy, Anticancer Research 10: 1169–1182 (1990).

Wu–Pong, S., Oligonucleotides: Opportunities for Drug Therapy and Research, Pharm. Tech.:102–114 (1994).

Westermann, P., et al., Inhibition of expression of SV40 virus large T–antigen by antisense Oligodeoxyribonucleotides, Biomed. Biochim. Acta 48(1): 85–93 (1989).

Herrenknecht et al., Characterization of Recombinant E–Cadherin (Uvomorulin) Expressed in Insect Cells, Journal of Cell Science, vol. Supp. 17, 1993, pp. 147–154.

M. Wheelock et all, Soluble 80–id Fragment of Cell–CAM 120/80 Disrupts Cell–Cell Adhesion, Journal of Cellular Biochemistry, vol. 34, No. 3, Jul. 1987.

M. Takeichi et al., Cadherin Cell Adhesion Receptors as a Morphogenetic Regulator, Science, vol. 251, No. 5000, Mar. 22, 1991, pp. 1451–1455.

M. Katayama et al., Soluble E–Cadherin Fragments Increased in Circulation of Cancer Patients, British Journal of Cancer, vol. 69, No. 3, Mar. 1994.

P. Karecla et al., Recognition of E–Cadherin on Epithelial Cells by the Mucosal T Cell Integrin AlphaM290beta7 (AlphaEbeta7), European J. Of Immunology, vol. 25, No. 3, Mar. 1995.

Roberts and O'Connell, "Binding of Intreapithelial Lymphocytes to Colon Cancer Cells is Mediated by HMLI and LFA1," A685, K.C. Ebert., Depts. Of Medicine and Surgery, UMDMJ–Robert Wood Johnson Medical School, New Brusnwick, NH (Apr. 1992).

Visser, Dabbagh, and Poppema, "Reactivity of Monoclonal Antibody B–ly7 with a Subset of Activated T Cells and T–Cell Lymphomas," Hematol Pathol 6(1):37–42 (1992).

Harris, W.J., et al., "Therapeutic Antibodies—the Comingof Age,"TIBTECH, 11:42–44, 1993 Feb.

Osband, M.E., et al., "Problems in the Investigational Study and Clinical Use of Cancer Immunotherapy," Immunology Today, 11(6):193–195, 1990.

Waldmann, T.A., "Monoclonal Antibodies in Diagnosis and Therapy," Science, 252:1657–1662, Jun. 1991.

Shirayoshi, Y. et al., "N–Linked Oligosaccharides Are Not Involved in the Function of a Cell–Cell Binding Glycoprotein E–Cadherin," Cell Structure and Function, 11:245–252, 1986.

Karecla, P.I., et al., "Recognition of E–Cadherin on Epithelial Cells by the Mucosal T Cell Integrin $\alpha_{M290}\beta 7$ ($\alpha E\beta 7$)," Eur. J. Immunol., 25:852–856, 1995.

Geiger, B. et al., "Cadherins," (1992) Annual Review of Cell Biology 8:307–32.

Takeichi M., "Cadherin Cell Adhesion Receptors as a Morphogenetic Regulator," (1991) Science 251:1451–1455.

Kemler, R., "From Cadherins to Catenins: Cytoplasmic Protein Interactions and Regulation of Cell Adhesion," (1993) Trends in Gastroenterology 9:317–321.

Nose, A. et al., "Localization of Specificity Determining Sites in Cadherin Cell Adhesion Molecules," (1990) Cell 61:147–155.

Kaiserlain D. et al., Expression, Function, and Regulation of the Intercellular Adhesion Molecule–1 (ICAM–1) on Human Intestinal Epithelial Cell Lines, (1991) Eur. J. of Immunol. 21(10):2415–2421.

Shimoyama Y. et al., "Cadherin Cell –Adhesion Molecules in Human Epithelial Tissues and Carcinomas," (1989) Cancer Research 49(8):2128–2133.

Vestweber D. et al., "Identification of a Putative Cell Adhesion Domain of Uvomorulin," (1985) EMBO J. 4:3393–3398.

Springer, T., "The Sensation and Regulation of Interactions with the Extracellular Environment: The Cell Biology of Lymphocyte Adhesion Receptors," (1990) Annual Review of Cell Biol. 6:359–402.

Cepek, K. et al., Adhesion Between Epithelial Cells and T Lymphocites Mediated by E–Cadherin and the $\alpha^E\beta7$ Integrin, Nature, vol. 372, Nov. 10, 1994, pp. 190–193.

Abstract; Roberts, A., et al., "Binding of Intraepithelial lymphocytes to colon cancer cells is mediated by HML1 and LFA1". Gastroenterology; 102:A685 (1992).

* cited by examiner

| I/X | $\alpha^L$ | $\alpha^M$ | $\alpha^X$ | $\alpha^1$ | $\alpha^2$ | $\alpha^3$ | $\alpha^4$ | $\alpha^5$ | $\alpha^6$ | $\alpha^7$ | $\alpha^8$ | $\alpha^V$ | $\alpha^{lib}$ | $\alpha^{ps2}$ |
|---|---|---|---|---|---|---|---|---|---|---|---|---|---|---|
| Removed | 52 | 51 | 52 | 51 | 51 | 50 | 50 | 49 | 51 | 49 | 47 | 48 | 47 | 46 |
| Full length | 53 | 52 | 54 | 51 | 52 | 49 | 50 | 49 | 52 | 48 | 46 | 49 | 48 | 42 |

Figure 3

SEQUENCE LISTING

<160> NUMBER OF SEQ ID NOS: 31

<210> SEQ ID NO 1
<211> LENGTH: 3933
<212> TYPE: DNA
<213> ORGANISM: Homo Sapiens
<220> FEATURE:
<221> NAME/KEY: CDS
<222> LOCATION: (126)...(3659)
<221> NAME/KEY: mat_peptide
<222> LOCATION: (180)...(3659)
<221> NAME/KEY: sig_peptide
<222> LOCATION: (126)...(179)

<400> SEQUENCE: 1

```
gaattccggc ccccgtgtct gggcgtccgc ctcctggcct cctggctgag gggaagctga      60
gtgggccacg gccatgtgt cgcactcgcc tcggctccca cacagccgcc tctgctccag     120 caagg atg tgg ctc ttc cac act ctg ctc tgc ata gcc agc ctg gcc ctg   170
      Met Trp Leu Phe His Thr Leu Leu Cys Ile Ala Ser Leu Ala Leu
          -15                 -10                  -5 ctg gcc gct ttc aat gtg gat gtg gcc cgg ccc tgg ctc acg ccc aag     218
Leu Ala Ala Phe Asn Val Asp Val Ala Arg Pro Trp Leu Thr Pro Lys
         1               5                  10 gga ggt gcc cct ttc gtg ctc agc tcc ctt ctg cac caa gac ccc agc     266
Gly Gly Ala Pro Phe Val Leu Ser Ser Leu Leu His Gln Asp Pro Ser
     15                  20                  25 acc aac cag acc tgg ctc ctg gtc acc agc ccc aga acc aag agg aca     314
Thr Asn Gln Thr Trp Leu Leu Val Thr Ser Pro Arg Thr Lys Arg Thr
 30                  35                  40                  45 cca ggg ccc ctc cat cga tgt tcc ctt gtc cag gat gaa atc ctt tgc     362
Pro Gly Pro Leu His Arg Cys Ser Leu Val Gln Asp Glu Ile Leu Cys
                 50                  55                  60 cat cct gta gag cat gtc ccc atc caa ggg gag gca ccg ggg agt gac     410
His Pro Val Glu His Val Pro Ile Gln Gly Glu Ala Pro Gly Ser Asp
             65                  70                  75 cgt tgt ccg gag cca cca cgg tgt ttt gat atg cat tca agt gct ggt     458
Arg Cys Pro Glu Pro Pro Arg Cys Phe Asp Met His Ser Ser Ala Gly
         80                  85                  90 ccg gcg cct cac agc ctc agc tca gaa ctc aca ggc acc tgt agc ctc     506
Pro Ala Pro His Ser Leu Ser Ser Glu Leu Thr Gly Thr Cys Ser Leu
     95                 100                 105 ctg ggc cct gac ctc cgt ccc cag gct cag gcc aac ttc ttc gac ctt     554
Leu Gly Pro Asp Leu Arg Pro Gln Ala Gln Ala Asn Phe Phe Asp Leu
110                 115                 120                 125 gaa aat ctc ctg gat cca gat gca cgt gtg gac act gga gac tgc tac     602
Glu Asn Leu Leu Asp Pro Asp Ala Arg Val Asp Thr Gly Asp Cys Tyr
                 130                 135                 140 agc aac aaa gaa ggc ggt gga gaa gac gat gtg aac aca gcc agg cag     650
Ser Asn Lys Glu Gly Gly Gly Glu Asp Asp Val Asn Thr Ala Arg Gln
             145                 150                 155 cgc cgg gct ctg gag aag gag gag gag gaa gac aag gag gag gag gaa     698
Arg Arg Ala Leu Glu Lys Glu Glu Glu Glu Asp Lys Glu Glu Glu Glu
```

-continued

|  |  |  |  |  |
|---|---|---|---|---|
| 160 | | 165 | | 170 |

| | | | | | | | | | | | | | | | |
|---|---|---|---|---|---|---|---|---|---|---|---|---|---|---|---|
| gac | gag | gag | gag | gag | gaa | gct | ggc | acc | gag | att | gcc | atc | atc | ctg | gat | 746
| Asp | Glu | Glu | Glu | Glu | Glu | Ala | Gly | Thr | Glu | Ile | Ala | Ile | Ile | Leu | Asp |
|  | 175 |  |  |  | 180 |  |  |  |  | 185 |  |  |  |  |  |

| ggc | tca | gga | agc | att | gat | ccc | cca | gac | ttt | cag | aga | gcc | aaa | gac | ttc | 794
| Gly | Ser | Gly | Ser | Ile | Asp | Pro | Pro | Asp | Phe | Gln | Arg | Ala | Lys | Asp | Phe |
| 190 |  |  |  |  | 195 |  |  |  |  | 200 |  |  |  |  | 205 |

| atc | tcc | aac | atg | atg | agg | aac | ttc | tat | gaa | aag | tgt | ttt | gag | tgc | aac | 842
| Ile | Ser | Asn | Met | Met | Arg | Asn | Phe | Tyr | Glu | Lys | Cys | Phe | Glu | Cys | Asn |
|  |  |  |  | 210 |  |  |  |  | 215 |  |  |  |  | 220 |  |

| ttt | gcc | ttg | gtg | cag | tat | gga | gga | gtg | atc | cag | act | gag | ttt | gac | ctt | 890
| Phe | Ala | Leu | Val | Gln | Tyr | Gly | Gly | Val | Ile | Gln | Thr | Glu | Phe | Asp | Leu |
|  |  |  |  | 225 |  |  |  |  | 230 |  |  |  |  | 235 |  |

| cgg | gac | agc | cag | gat | gtg | atg | gcc | tcc | ctc | gcc | aga | gtc | cag | aac | atc | 938
| Arg | Asp | Ser | Gln | Asp | Val | Met | Ala | Ser | Leu | Ala | Arg | Val | Gln | Asn | Ile |
|  |  |  | 240 |  |  |  |  | 245 |  |  |  |  | 250 |  |  |

| act | caa | gtg | ggg | agt | gtc | acc | aag | act | gcc | tca | gcc | atg | caa | cac | gtc | 986
| Thr | Gln | Val | Gly | Ser | Val | Thr | Lys | Thr | Ala | Ser | Ala | Met | Gln | His | Val |
|  | 255 |  |  |  |  | 260 |  |  |  |  | 265 |  |  |  |  |

| tta | gac | agc | atc | ttc | acc | tca | agc | cac | ggc | tcc | agg | aga | aag | gca | tcc | 1034
| Leu | Asp | Ser | Ile | Phe | Thr | Ser | Ser | His | Gly | Ser | Arg | Arg | Lys | Ala | Ser |
| 270 |  |  |  |  | 275 |  |  |  |  | 280 |  |  |  |  | 285 |

| aag | gtc | atg | gtg | gtg | ctc | acc | gat | ggt | ggc | ata | ttc | gag | gac | ccc | ctc | 1082
| Lys | Val | Met | Val | Val | Leu | Thr | Asp | Gly | Gly | Ile | Phe | Glu | Asp | Pro | Leu |
|  |  |  |  | 290 |  |  |  |  | 295 |  |  |  |  | 300 |  |

| aac | ctt | acg | aca | gtc | atc | aac | tcc | ccc | aaa | atg | cag | ggt | gtt | gag | cgc | 1130
| Asn | Leu | Thr | Thr | Val | Ile | Asn | Ser | Pro | Lys | Met | Gln | Gly | Val | Glu | Arg |
|  |  |  | 305 |  |  |  |  | 310 |  |  |  |  | 315 |  |  |

| ttt | gcc | att | ggg | gtg | gga | gaa | gaa | ttt | aag | agt | gct | agg | act | gcg | agg | 1178
| Phe | Ala | Ile | Gly | Val | Gly | Glu | Glu | Phe | Lys | Ser | Ala | Arg | Thr | Ala | Arg |
|  | 320 |  |  |  |  | 325 |  |  |  |  | 330 |  |  |  |  |

| gaa | ctg | aac | ctg | atc | gcc | tca | gac | ccg | gat | gag | acc | cat | gct | ttc | aag | 1226
| Glu | Leu | Asn | Leu | Ile | Ala | Ser | Asp | Pro | Asp | Glu | Thr | His | Ala | Phe | Lys |
|  | 335 |  |  |  |  | 340 |  |  |  |  | 345 |  |  |  |  |

| gtg | acc | aac | tac | atg | gcg | ctg | gat | ggg | ctg | ctg | agc | aaa | ctg | cgg | tac | 1274
| Val | Thr | Asn | Tyr | Met | Ala | Leu | Asp | Gly | Leu | Leu | Ser | Lys | Leu | Arg | Tyr |
| 350 |  |  |  |  | 355 |  |  |  |  | 360 |  |  |  |  | 365 |

| aac | atc | atc | agc | atg | gaa | ggc | acg | gtt | gga | gac | gcc | ctt | cac | tac | cag | 1322
| Asn | Ile | Ile | Ser | Met | Glu | Gly | Thr | Val | Gly | Asp | Ala | Leu | His | Tyr | Gln |
|  |  |  | 370 |  |  |  |  | 375 |  |  |  |  | 380 |  |  |

| ctg | gca | cag | att | ggc | ttc | agt | gct | cag | atc | ctg | gat | gag | cgg | cag | gtg | 1370
| Leu | Ala | Gln | Ile | Gly | Phe | Ser | Ala | Gln | Ile | Leu | Asp | Glu | Arg | Gln | Val |
|  |  | 385 |  |  |  |  | 390 |  |  |  |  | 395 |  |  |  |

| ctg | ctc | ggc | gcc | gtc | ggg | gcc | ttt | gac | tgg | tcc | gga | ggg | gcg | ttg | ctc | 1418
| Leu | Leu | Gly | Ala | Val | Gly | Ala | Phe | Asp | Trp | Ser | Gly | Gly | Ala | Leu | Leu |
|  |  | 400 |  |  |  |  | 405 |  |  |  |  | 410 |  |  |  |

| tac | gac | aca | cgc | agc | cgc | cgg | ggc | cgc | ttc | ctg | aac | cag | aca | gcg | gcg | 1466
| Tyr | Asp | Thr | Arg | Ser | Arg | Arg | Gly | Arg | Phe | Leu | Asn | Gln | Thr | Ala | Ala |
|  | 415 |  |  |  |  | 420 |  |  |  |  | 425 |  |  |  |  |

| gcg | gcg | gca | gac | gcg | gag | gct | gcg | cag | tac | agc | tac | ctg | ggt | tac | gct | 1514
| Ala | Ala | Ala | Asp | Ala | Glu | Ala | Ala | Gln | Tyr | Ser | Tyr | Leu | Gly | Tyr | Ala |
| 430 |  |  |  |  | 435 |  |  |  |  | 440 |  |  |  |  | 445 |

| gtg | gcc | gtg | ctg | cac | aag | acc | tgc | agc | ctc | tcc | tac | gtc | gcg | ggg | gct | 1562
| Val | Ala | Val | Leu | His | Lys | Thr | Cys | Ser | Leu | Ser | Tyr | Val | Ala | Gly | Ala |
|  |  |  |  | 450 |  |  |  |  | 455 |  |  |  |  | 460 |  |

| cca | cag | tac | aaa | cat | cat | ggg | gcc | gtg | ttt | gag | ctc | cag | aag | gag | ggc | 1610
| Pro | Gln | Tyr | Lys | His | His | Gly | Ala | Val | Phe | Glu | Leu | Gln | Lys | Glu | Gly |
|  |  | 465 |  |  |  |  | 470 |  |  |  |  | 475 |  |  |  |

| aga | gag | gcc | agc | ttc | ctg | cca | gtg | ctg | gag | gga | gag | cag | atg | ggg | tcc | 1658

```
                                                                -continued

Arg Glu Ala Ser Phe Leu Pro Val Leu Glu Gly Glu Gln Met Gly Ser
            480                 485                 490 tat ttt ggc tct gag ctg tgc cct gtg gac att gac atg gat gga agc      1706
Tyr Phe Gly Ser Glu Leu Cys Pro Val Asp Ile Asp Met Asp Gly Ser
495                 500                 505 acg gac ttc ttg ctg gtg gct gct cca ttt tac cac gtt cat gga gaa      1754
Thr Asp Phe Leu Leu Val Ala Ala Pro Phe Tyr His Val His Gly Glu
510                 515                 520                 525 gaa ggc aga gtc tac gtg tac cgt ctc agc gag cag gat ggt tct ttc      1802
Glu Gly Arg Val Tyr Val Tyr Arg Leu Ser Glu Gln Asp Gly Ser Phe
                530                 535                 540 tcc ttg gca cgc ata ctg agt ggg cac ccc ggg ttc acc aat gcc cgc      1850
Ser Leu Ala Arg Ile Leu Ser Gly His Pro Gly Phe Thr Asn Ala Arg
            545                 550                 555 ttt ggc ttt gcc atg gcg gct atg ggg gat ctc agt cag gat aag ctc      1898
Phe Gly Phe Ala Met Ala Ala Met Gly Asp Leu Ser Gln Asp Lys Leu
        560                 565                 570 aca gat gtg gcc atc ggg gcc ccc ctg gaa ggt ttt ggg gca gat gat      1946
Thr Asp Val Ala Ile Gly Ala Pro Leu Glu Gly Phe Gly Ala Asp Asp
575                 580                 585 ggt gcc agc ttc ggc agt gtg tat atc tac aat gga cac tgg gac ggc      1994
Gly Ala Ser Phe Gly Ser Val Tyr Ile Tyr Asn Gly His Trp Asp Gly
590                 595                 600                 605 ctc tcc gcc agc ccc tcg cag cgg atc aga gcc tcc acg gtg gcc cca      2042
Leu Ser Ala Ser Pro Ser Gln Arg Ile Arg Ala Ser Thr Val Ala Pro
                610                 615                 620 gga ctc cag tac ttc ggc atg tcc atg gct ggt ggc ttt gat att agt      2090
Gly Leu Gln Tyr Phe Gly Met Ser Met Ala Gly Gly Phe Asp Ile Ser
            625                 630                 635 ggc gac ggc ctt gcc gac atc acc gtg ggc act ctg ggc cag gcg gtt      2138
Gly Asp Gly Leu Ala Asp Ile Thr Val Gly Thr Leu Gly Gln Ala Val
        640                 645                 650 gtg ttc cgc tcc cgg cct gtg gtt cgc ctg aag gtc tcc atg gcc ttc      2186
Val Phe Arg Ser Arg Pro Val Val Arg Leu Lys Val Ser Met Ala Phe
655                 660                 665 acc ccc agc gca ctg ccc atc ggc ttc aac ggc gtc gtg aat gtc cgt      2234
Thr Pro Ser Ala Leu Pro Ile Gly Phe Asn Gly Val Val Asn Val Arg
670                 675                 680                 685 tta tgt ttt gaa atc agc tct gta acc aca gcc tct gag tca ggc ctc      2282
Leu Cys Phe Glu Ile Ser Ser Val Thr Thr Ala Ser Glu Ser Gly Leu
                690                 695                 700 cgt gag gca ctt ctc aac ttc acg ctg gat gtg gat gtg ggg aag cag      2330
Arg Glu Ala Leu Leu Asn Phe Thr Leu Asp Val Asp Val Gly Lys Gln
            705                 710                 715 agg aga cgg ctg cag tgt tca gac gta aga agc tgt ctg ggc tgc ctg      2378
Arg Arg Arg Leu Gln Cys Ser Asp Val Arg Ser Cys Leu Gly Cys Leu
        720                 725                 730 agg gag tgg agc agc gga tcc cag ctt tgt gag gac ctc ctc ctc atg      2426
Arg Glu Trp Ser Ser Gly Ser Gln Leu Cys Glu Asp Leu Leu Leu Met
735                 740                 745 ccc aca gag gga gag ctc tgt gag gag gac tgc ttc tcc aat gcc agt      2474
Pro Thr Glu Gly Glu Leu Cys Glu Glu Asp Cys Phe Ser Asn Ala Ser
750                 755                 760                 765 gtc aaa gtc agc tac cag ctc cag acc cct gag gga cag acg gac cat      2522
Val Lys Val Ser Tyr Gln Leu Gln Thr Pro Glu Gly Gln Thr Asp His
                770                 775                 780 ccc cag ccc atc ctg gac cgc tac act gag ccc ttt gcc atc ttc cag      2570
Pro Gln Pro Ile Leu Asp Arg Tyr Thr Glu Pro Phe Ala Ile Phe Gln
            785                 790                 795
```

```
ctg ccc tat gag aag gcc tgc aag aat aag ctg ttt tgt gtc gca gaa      2618
Leu Pro Tyr Glu Lys Ala Cys Lys Asn Lys Leu Phe Cys Val Ala Glu
        800                 805                 810 tta cag ttg gcc acc acc gtc tct cag cag gag ttg gtg gtg ggt ctc      2666
Leu Gln Leu Ala Thr Thr Val Ser Gln Gln Glu Leu Val Val Gly Leu
    815                 820                 825 aca aag gag ctg acc ctg aac att aac cta act aac tcc ggg gaa gat      2714
Thr Lys Glu Leu Thr Leu Asn Ile Asn Leu Thr Asn Ser Gly Glu Asp
830                 835                 840                 845 tcc tac atg aca agc atg gcc ttg aat tac ccc aga aac ctg cag ttg      2762
Ser Tyr Met Thr Ser Met Ala Leu Asn Tyr Pro Arg Asn Leu Gln Leu
                850                 855                 860 aag agg atg caa aag cct ccc tct cca aac att cag tgt gat gac cct      2810
Lys Arg Met Gln Lys Pro Pro Ser Pro Asn Ile Gln Cys Asp Asp Pro
            865                 870                 875 cag ccg gtt gct tct gtc ctg atc atg aac tgc agg att ggt cac ccc      2858
Gln Pro Val Ala Ser Val Leu Ile Met Asn Cys Arg Ile Gly His Pro
        880                 885                 890 gtc ctc aag agg tca tct gct cat gtt tca gtc gtt tgg cag cta gag      2906
Val Leu Lys Arg Ser Ser Ala His Val Ser Val Val Trp Gln Leu Glu
    895                 900                 905 gag aat gcc ttt cca aac agg aca gca gac atc act gtg act gtc acc      2954
Glu Asn Ala Phe Pro Asn Arg Thr Ala Asp Ile Thr Val Thr Val Thr
910                 915                 920                 925 aat tcc aat gaa aga cgg tct ttg gcc aac gag acc cac acc ctt caa      3002
Asn Ser Asn Glu Arg Arg Ser Leu Ala Asn Glu Thr His Thr Leu Gln
                930                 935                 940 ttc agg cat ggc ttc gtt gca gtt ctg tcc aaa cca tcc ata atg tac      3050
Phe Arg His Gly Phe Val Ala Val Leu Ser Lys Pro Ser Ile Met Tyr
            945                 950                 955 gtg aac aca ggc cag ggg ctt tct cac cac aaa gaa ttc ctc ttc cat      3098
Val Asn Thr Gly Gln Gly Leu Ser His His Lys Glu Phe Leu Phe His
        960                 965                 970 gta cat ggg gag aac ctc ttt gga gca gaa tac cag ttg caa att tgc      3146
Val His Gly Glu Asn Leu Phe Gly Ala Glu Tyr Gln Leu Gln Ile Cys
    975                 980                 985 gtc cca acc aaa tta cga ggt ctc cag gtt gca gca gtg aag aag ctg      3194
Val Pro Thr Lys Leu Arg Gly Leu Gln Val Ala Ala Val Lys Lys Leu
990                 995                 1000                1005 acg agg act cag gcc tcc acg gtg tgc acc tgg agt cag gag cgc gct      3242
Thr Arg Thr Gln Ala Ser Thr Val Cys Thr Trp Ser Gln Glu Arg Ala
                1010                1015                1020 tgt gcg tac agt tcg gtt cag cat gtg gaa gaa tgg cat tca gtg agc      3290
Cys Ala Tyr Ser Ser Val Gln His Val Glu Glu Trp His Ser Val Ser
            1025                1030                1035 tgt gtc atc gct tca gat aaa gaa aat gtc acc gtg gct gca gag atc      3338
Cys Val Ile Ala Ser Asp Lys Glu Asn Val Thr Val Ala Ala Glu Ile
        1040                1045                1050 tcc tgg gat cac tct gag gag tta cta aaa gat gta act gaa ctg cag      3386
Ser Trp Asp His Ser Glu Glu Leu Leu Lys Asp Val Thr Glu Leu Gln
    1055                1060                1065 atc ctt ggt gaa ata tct ttc aac aaa tct cta tat gag gga ctg aat      3434
Ile Leu Gly Glu Ile Ser Phe Asn Lys Ser Leu Tyr Glu Gly Leu Asn
1070                1075                1080                1085 gca gag aac cac aga act aag atc act gtc gtc ttc ctg aaa gat gag      3482
Ala Glu Asn His Arg Thr Lys Ile Thr Val Val Phe Leu Lys Asp Glu
                1090                1095                1100 aag tac cat tct ttg cct atc atc att aaa ggc agc gtt ggt gga ctt      3530
Lys Tyr His Ser Leu Pro Ile Ile Ile Lys Gly Ser Val Gly Gly Leu
            1105                1110                1115
```

-continued

```
ctg gtg ttg atc gtg att ctg gtc atc ctg ttc aag tgt ggc ttt ttt    3578
Leu Val Leu Ile Val Ile Leu Val Ile Leu Phe Lys Cys Gly Phe Phe
        1120            1125            1130 aaa aga aaa tat caa caa ctg aac ttg gag agc atc agg aag gcc cag    3626
Lys Arg Lys Tyr Gln Gln Leu Asn Leu Glu Ser Ile Arg Lys Ala Gln
    1135            1140            1145 ctg aaa tca gag aat ctg ctc gaa gaa gag aat taggacctgc tatccactgg  3679
Leu Lys Ser Glu Asn Leu Leu Glu Glu Glu Asn
1150            1155            1160 gagaggctat cagccagtcc tgggacttgg agacccagca tcctttgcat tacttttcc   3739 ttcaggatga tctagagcag catggagctg ttggtagaat attagttttt aaccatacat  3799
tgtcccaaaa gtgtctgtgc attgtgcaaa agtaaactt aggaaacatt tggtattaaa   3859
taaatttaca cttttctttg caaaaaaaaa aaaaaaaaa aaaaaaaaa aaaaaaaaa     3919 aaaaaccgga attc                                                     3933
```

<210> SEQ ID NO 2
<211> LENGTH: 1178
<212> TYPE: PRT
<213> ORGANISM: Homo Sapiens
<220> FEATURE:
<221> NAME/KEY: SIGNAL
<222> LOCATION: (-18)...(-1)

<400> SEQUENCE: 2

```
Met Trp Leu Phe His Thr Leu Leu Cys Ile Ala Ser Leu Ala Leu Leu
            -15                 -10                  -5

Ala Ala Phe Asn Val Asp Val Ala Arg Pro Trp Leu Thr Pro Lys Gly
         1               5                  10

Gly Ala Pro Phe Val Leu Ser Ser Leu Leu His Gln Asp Pro Ser Thr
15                  20                  25                  30

Asn Gln Thr Trp Leu Leu Val Thr Ser Pro Arg Thr Lys Arg Thr Pro
                35                  40                  45

Gly Pro Leu His Arg Cys Ser Leu Val Gln Asp Glu Ile Leu Cys His
            50                  55                  60

Pro Val Glu His Val Pro Ile Gln Gly Glu Ala Pro Gly Ser Asp Arg
65                  70                  75

Cys Pro Glu Pro Pro Arg Cys Phe Asp Met His Ser Ser Ala Gly Pro
        80                  85                  90

Ala Pro His Ser Leu Ser Ser Glu Leu Thr Gly Thr Cys Ser Leu Leu
95                  100                 105                 110

Gly Pro Asp Leu Arg Pro Gln Ala Gln Ala Asn Phe Phe Asp Leu Glu
                115                 120                 125

Asn Leu Leu Asp Pro Asp Ala Arg Val Asp Thr Gly Asp Cys Tyr Ser
            130                 135                 140

Asn Lys Glu Gly Gly Glu Asp Val Asn Thr Ala Arg Gln Arg
145                 150                 155

Arg Ala Leu Glu Lys Glu Glu Glu Asp Lys Glu Glu Glu Asp
        160                 165                 170

Glu Glu Glu Glu Ala Gly Thr Glu Ile Ala Ile Ile Leu Asp Gly
175                 180                 185                 190

Ser Gly Ser Ile Asp Pro Pro Asp Phe Gln Arg Ala Lys Asp Phe Ile
                195                 200                 205

Ser Asn Met Met Arg Asn Phe Tyr Glu Lys Cys Phe Glu Cys Asn Phe
            210                 215                 220
```

```
Ala Leu Val Gln Tyr Gly Gly Val Ile Gln Thr Glu Phe Asp Leu Arg
            225                 230                 235

Asp Ser Gln Asp Val Met Ala Ser Leu Ala Arg Val Gln Asn Ile Thr
240                 245                 250

Gln Val Gly Ser Val Thr Lys Thr Ala Ser Ala Met Gln His Val Leu
255                 260                 265                 270

Asp Ser Ile Phe Thr Ser Ser His Gly Ser Arg Arg Lys Ala Ser Lys
                275                 280                 285

Val Met Val Val Leu Thr Asp Gly Gly Ile Phe Glu Asp Pro Leu Asn
            290                 295                 300

Leu Thr Thr Val Ile Asn Ser Pro Lys Met Gln Gly Val Glu Arg Phe
            305                 310                 315

Ala Ile Gly Val Gly Glu Glu Phe Lys Ser Ala Arg Thr Ala Arg Glu
            320                 325                 330

Leu Asn Leu Ile Ala Ser Asp Pro Asp Glu Thr His Ala Phe Lys Val
335                 340                 345                 350

Thr Asn Tyr Met Ala Leu Asp Gly Leu Leu Ser Lys Leu Arg Tyr Asn
                355                 360                 365

Ile Ile Ser Met Glu Gly Thr Val Gly Asp Ala Leu His Tyr Gln Leu
            370                 375                 380

Ala Gln Ile Gly Phe Ser Ala Gln Ile Leu Asp Glu Arg Gln Val Leu
            385                 390                 395

Leu Gly Ala Val Gly Ala Phe Asp Trp Ser Gly Gly Ala Leu Leu Tyr
400                 405                 410

Asp Thr Arg Ser Arg Arg Gly Arg Phe Leu Asn Gln Thr Ala Ala Ala
415                 420                 425                 430

Ala Ala Asp Ala Glu Ala Ala Gln Tyr Ser Tyr Leu Gly Tyr Ala Val
                435                 440                 445

Ala Val Leu His Lys Thr Cys Ser Leu Ser Tyr Val Ala Gly Ala Pro
            450                 455                 460

Gln Tyr Lys His His Gly Ala Val Phe Glu Leu Gln Lys Glu Gly Arg
            465                 470                 475

Glu Ala Ser Phe Leu Pro Val Leu Glu Gly Glu Gln Met Gly Ser Tyr
480                 485                 490

Phe Gly Ser Glu Leu Cys Pro Val Asp Ile Asp Met Asp Gly Ser Thr
495                 500                 505                 510

Asp Phe Leu Leu Val Ala Ala Pro Phe Tyr His Val His Gly Glu Glu
                515                 520                 525

Gly Arg Val Tyr Val Tyr Arg Leu Ser Glu Gln Asp Gly Ser Phe Ser
            530                 535                 540

Leu Ala Arg Ile Leu Ser Gly His Pro Gly Phe Thr Asn Ala Arg Phe
            545                 550                 555

Gly Phe Ala Met Ala Ala Met Gly Asp Leu Ser Gln Asp Lys Leu Thr
560                 565                 570

Asp Val Ala Ile Gly Ala Pro Leu Glu Gly Phe Gly Ala Asp Asp Gly
575                 580                 585                 590

Ala Ser Phe Gly Ser Val Tyr Ile Tyr Asn Gly His Trp Asp Gly Leu
                595                 600                 605

Ser Ala Ser Pro Ser Gln Arg Ile Arg Ala Ser Thr Val Ala Pro Gly
            610                 615                 620

Leu Gln Tyr Phe Gly Met Ser Met Ala Gly Gly Phe Asp Ile Ser Gly
            625                 630                 635

Asp Gly Leu Ala Asp Ile Thr Val Gly Thr Leu Gly Gln Ala Val Val
```

-continued

```
          640                 645                 650
Phe Arg Ser Arg Pro Val Val Arg Leu Lys Val Ser Met Ala Phe Thr
655                 660                 665                 670
Pro Ser Ala Leu Pro Ile Gly Phe Asn Gly Val Asn Val Arg Leu
                675                 680                 685
Cys Phe Glu Ile Ser Ser Val Thr Thr Ala Ser Glu Ser Gly Leu Arg
                690                 695                 700
Glu Ala Leu Leu Asn Phe Thr Leu Asp Val Asp Val Gly Lys Gln Arg
                705                 710                 715
Arg Arg Leu Gln Cys Ser Asp Val Arg Ser Cys Leu Gly Cys Leu Arg
720                 725                 730
Glu Trp Ser Ser Gly Ser Gln Leu Cys Glu Asp Leu Leu Met Pro
735                 740                 745                 750
Thr Glu Gly Glu Leu Cys Glu Glu Asp Cys Phe Ser Asn Ala Ser Val
                755                 760                 765
Lys Val Ser Tyr Gln Leu Gln Thr Pro Glu Gly Gln Thr Asp His Pro
                770                 775                 780
Gln Pro Ile Leu Asp Arg Tyr Thr Glu Pro Phe Ala Ile Phe Gln Leu
                785                 790                 795
Pro Tyr Glu Lys Ala Cys Lys Asn Lys Leu Phe Cys Val Ala Glu Leu
                800                 805                 810
Gln Leu Ala Thr Thr Val Ser Gln Gln Glu Leu Val Val Gly Leu Thr
815                 820                 825                 830
Lys Glu Leu Thr Leu Asn Ile Asn Leu Thr Asn Ser Gly Glu Asp Ser
                835                 840                 845
Tyr Met Thr Ser Met Ala Leu Asn Tyr Pro Arg Asn Leu Gln Leu Lys
                850                 855                 860
Arg Met Gln Lys Pro Pro Ser Pro Asn Ile Gln Cys Asp Asp Pro Gln
                865                 870                 875
Pro Val Ala Ser Val Leu Ile Met Asn Cys Arg Ile Gly His Pro Val
                880                 885                 890
Leu Lys Arg Ser Ser Ala His Val Ser Val Val Trp Gln Leu Glu Glu
895                 900                 905                 910
Asn Ala Phe Pro Asn Arg Thr Ala Asp Ile Thr Val Thr Val Thr Asn
                915                 920                 925
Ser Asn Glu Arg Arg Ser Leu Ala Asn Glu Thr His Thr Leu Gln Phe
                930                 935                 940
Arg His Gly Phe Val Ala Val Leu Ser Lys Pro Ser Ile Met Tyr Val
                945                 950                 955
Asn Thr Gly Gln Gly Leu Ser His His Lys Glu Phe Leu Phe His Val
                960                 965                 970
His Gly Glu Asn Leu Phe Gly Ala Glu Tyr Gln Leu Gln Ile Cys Val
975                 980                 985                 990
Pro Thr Lys Leu Arg Gly Leu Gln Val Ala Ala Val Lys Lys Leu Thr
                995                 1000                1005
Arg Thr Gln Ala Ser Thr Val Cys Thr Trp Ser Gln Glu Arg Ala Cys
                1010                1015                1020
Ala Tyr Ser Ser Val Gln His Val Glu Glu Trp His Ser Val Ser Cys
                1025                1030                1035
Val Ile Ala Ser Asp Lys Glu Asn Val Thr Val Ala Ala Glu Ile Ser
                1040                1045                1050
Trp Asp His Ser Glu Glu Leu Leu Lys Asp Val Thr Glu Leu Gln Ile
1055                1060                1065                107
```

```
Leu Gly Glu Ile Ser Phe Asn Lys Ser Leu Tyr Glu Gly Leu Asn Ala
            1075                1080                1085

Glu Asn His Arg Thr Lys Ile Thr Val Val Phe Leu Lys Asp Glu Lys
        1090                1095                1100

Tyr His Ser Leu Pro Ile Ile Ile Lys Gly Ser Val Gly Gly Leu Leu
    1105                1110                1115

Val Leu Ile Val Ile Leu Val Ile Leu Phe Lys Cys Gly Phe Phe Lys
        1120                1125                1130

Arg Lys Tyr Gln Gln Leu Asn Leu Glu Ser Ile Arg Lys Ala Gln Leu
1135                1140                1145                115

Lys Ser Glu Asn Leu Leu Glu Glu Glu Asn
            1155                1160

<210> SEQ ID NO 3
<211> LENGTH: 165
<212> TYPE: DNA
<213> ORGANISM: Homo Sapiens

<400> SEQUENCE: 3
gaaaatctcc tggatccaga tgcacgtgtg gacactggag actgctacag caacaaagaa      60
ggcggtggag aagacgatgt gaacacagcc aggcagcgcc gggctctgga gaaggaggag     120
gaggaagaca aggaggagga ggaagacgag gaggaggagg aagct                     165

<210> SEQ ID NO 4
<211> LENGTH: 55
<212> TYPE: PRT
<213> ORGANISM: Homo Sapiens

<400> SEQUENCE: 4

Glu Asn Leu Leu Asp Pro Asp Ala Arg Val Asp Thr Gly Asp Cys Tyr
1               5                   10                  15

Ser Asn Lys Glu Gly Gly Gly Glu Asp Asp Val Asn Thr Ala Arg Gln
            20                  25                  30

Arg Arg Ala Leu Glu Lys Glu Glu Glu Asp Lys Glu Glu Glu Glu Glu
        35                  40                  45

Asp Glu Glu Glu Glu Glu Ala
    50                  55

<210> SEQ ID NO 5
<211> LENGTH: 21
<212> TYPE: PRT
<213> ORGANISM: Homo Sapiens

<400> SEQUENCE: 5

Ala Leu Glu Lys Glu Glu Glu Glu Asp Lys Glu Glu Glu Glu Asp Glu
1               5                   10                  15

Glu Glu Glu Glu Ala
            20

<210> SEQ ID NO 6
<211> LENGTH: 34
<212> TYPE: PRT
<213> ORGANISM: Homo Sapiens

<400> SEQUENCE: 6

Glu Asn Leu Leu Asp Pro Asp Ala Arg Val Asp Thr Gly Asp Cys Tyr
1               5                   10                  15

Ser Asn Lys Glu Gly Gly Gly Glu Asp Asp Val Asn Thr Ala Arg Gln
```

```
                20                  25                  30
Arg Arg

<210> SEQ ID NO 7
<211> LENGTH: 102
<212> TYPE: DNA
<213> ORGANISM: Homo Sapiens

<400> SEQUENCE: 7
gaaaatctcc tggatccaga tgcacgtgtg gacactggag actgctacag caacaaagaa      60
ggcggtggag aagacgatgt gaacacagcc aggcagcgcc gg                        102

<210> SEQ ID NO 8
<211> LENGTH: 10
<212> TYPE: PRT
<213> ORGANISM: Homo Sapiens

<400> SEQUENCE: 8

Glu Lys Glu Glu Glu Glu Asp Lys Glu Glu
 1               5                  10

<210> SEQ ID NO 9
<211> LENGTH: 10
<212> TYPE: PRT
<213> ORGANISM: Homo Sapiens

<400> SEQUENCE: 9

Lys Glu Glu Glu Glu Asp Lys Glu Glu Glu
 1               5                  10

<210> SEQ ID NO 10
<211> LENGTH: 10
<212> TYPE: PRT
<213> ORGANISM: Homo Sapiens

<400> SEQUENCE: 10

Glu Glu Glu Glu Asp Lys Glu Glu Glu Glu
 1               5                  10

<210> SEQ ID NO 11
<211> LENGTH: 10
<212> TYPE: PRT
<213> ORGANISM: Homo Sapiens

<400> SEQUENCE: 11

Glu Glu Glu Asp Lys Glu Glu Glu Glu Asp
 1               5                  10

<210> SEQ ID NO 12
<211> LENGTH: 10
<212> TYPE: PRT
<213> ORGANISM: Homo Sapiens

<400> SEQUENCE: 12

Glu Glu Asp Lys Glu Glu Glu Glu Asp Glu
 1               5                  10

<210> SEQ ID NO 13
<211> LENGTH: 10
<212> TYPE: PRT
<213> ORGANISM: Homo Sapiens

<400> SEQUENCE: 13
```

```
Glu Asp Lys Glu Glu Glu Glu Asp Glu Glu
  1               5                  10
```

<210> SEQ ID NO 14
<211> LENGTH: 10
<212> TYPE: PRT
<213> ORGANISM: Homo Sapiens

<400> SEQUENCE: 14

```
Asp Lys Glu Glu Glu Glu Asp Glu Glu Glu
  1               5                  10
```

<210> SEQ ID NO 15
<211> LENGTH: 10
<212> TYPE: PRT
<213> ORGANISM: Homo Sapiens

<400> SEQUENCE: 15

```
Lys Glu Glu Glu Glu Asp Glu Glu Glu Glu
  1               5                  10
```

<210> SEQ ID NO 16
<211> LENGTH: 10
<212> TYPE: PRT
<213> ORGANISM: Homo Sapiens

<400> SEQUENCE: 16

```
Glu Glu Glu Glu Asp Glu Glu Glu Glu Glu
  1               5                  10
```

<210> SEQ ID NO 17
<211> LENGTH: 10
<212> TYPE: PRT
<213> ORGANISM: Homo Sapiens

<400> SEQUENCE: 17

```
Ala Leu Glu Lys Glu Glu Glu Glu Asp Lys
  1               5                  10
```

<210> SEQ ID NO 18
<211> LENGTH: 14
<212> TYPE: PRT
<213> ORGANISM: Homo Sapiens

<400> SEQUENCE: 18

```
Glu Glu Asp Lys Glu Glu Glu Glu Asp Glu Glu Glu Glu
  1               5                  10
```

<210> SEQ ID NO 19
<211> LENGTH: 14
<212> TYPE: PRT
<213> ORGANISM: Homo Sapiens

<400> SEQUENCE: 19

```
Ala Leu Glu Lys Glu Glu Glu Glu Asp Lys Glu Glu Glu Glu
  1               5                  10
```

<210> SEQ ID NO 20
<211> LENGTH: 15
<212> TYPE: PRT
<213> ORGANISM: Homo Sapiens

<400> SEQUENCE: 20

```
Glu Lys Glu Glu Glu Glu Asp Lys Glu Glu Glu Glu Asp Glu Glu
  1               5                  10                  15
```

<210> SEQ ID NO 21
<211> LENGTH: 20
<212> TYPE: PRT
<213> ORGANISM: Homo Sapiens

<400> SEQUENCE: 21

Ala Leu Glu Lys Glu Glu Glu Asp Lys Glu Glu Glu Asp Glu
1               5                   10                  15

Glu Glu Glu Glu
            20

<210> SEQ ID NO 22
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 22

Glu Lys Glu Glu Glu Asp Glu Glu Glu Glu Glu
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 23

Asp Lys Asp Asp Asp Asp Asp Asp Asp Asp Asp Asp
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 24

Glu Asp Glu Glu Glu Glu Glu Glu Glu Glu Glu Glu
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 25

Glu Asn Glu Glu Glu Glu Asp Asn Glu Glu Glu Glu Asp
1               5                   10

<210> SEQ ID NO 26
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 26

Ala Leu Glu Lys Glu Glu Glu Glu Asp Lys Glu Glu Glu Glu Asp Glu
1               5                   10                  15

```
Glu Glu Glu Glu Cys
            20

<210> SEQ ID NO 27
<211> LENGTH: 9
<212> TYPE: PRT
<213> ORGANISM: Homo Sapiens
<220> FEATURE:
<221> NAME/KEY: VARIANT
<222> LOCATION: (2)...(4)
<221> NAME/KEY: VARIANT
<222> LOCATION: (6)...(8)

<400> SEQUENCE: 27

Asp Xaa Xaa Xaa Asp Xaa Xaa Xaa Asp
1               5

<210> SEQ ID NO 28
<211> LENGTH: 5
<212> TYPE: PRT
<213> ORGANISM: Drosophila Melanogaster

<400> SEQUENCE: 28

Gly Phe Phe Asn Arg
1               5

<210> SEQ ID NO 29
<211> LENGTH: 5
<212> TYPE: PRT
<213> ORGANISM: Gallus Gallus

<400> SEQUENCE: 29

Gly Phe Phe Asp Arg
1               5

<210> SEQ ID NO 30
<211> LENGTH: 5
<212> TYPE: PRT
<213> ORGANISM: Cricetinae gen. sp. (Hamster)

<400> SEQUENCE: 30

Asp Phe Phe Lys Pro
1               5

<210> SEQ ID NO 31
<211> LENGTH: 5
<212> TYPE: PRT
<213> ORGANISM: Homo Sapiens

<400> SEQUENCE: 31

Gly Phe Phe Lys Arg
1               5
```

METHOD OF TREATING ULCERATIVE COLITIS OR CROHN'S DISEASE BY ADMINISTERING AN ANTIBODY TO $\alpha^E\beta^7$ INTEGRIN

RELATED APPLICATIONS

This application is a divisional of application Ser. No. 08/879,338, filed Jun. 20, 1997, now U.S. Pat. No. 6,063,916 entitled "ANTIBODIES TO INTEGRIN ALPHA SUBUNIT (AS AMENDED)," and now which is a divisional of U.S. Ser. No. 08/663,731, filed Jun. 14, 1996, now U.S. Pat. No. 6,057,425 entitled "NOVEL INTEGRIN ALPHA SUBUNIT" now which is a divisional of U.S. Ser. No. 08/199,776, filed Feb. 18, 1994, entitled "NOVEL INTEGRIN ALPHA SUBUNIT" issued Jan. 14, 1997, as U.S. Pat. No. 5,594,120.

GOVERNMENT SUPPORT

This invention was made in part with government support under grant numbers R01CA47724, R29GM49342 and K11AI00903 from the National Institutes of Health.

FIELD OF THE INVENTION

This invention relates to a novel integrin alpha chain; functionally-equivalent peptide fragments and analogs thereof; oligonucleotides encoding the peptide fragments and analogs; vectors containing and cell lines expressing the novel peptides; and methods for using the peptide fragments, analogs and oligonucleotides.

BACKGROUND OF THE INVENTION

The integrin mediated adhesive interactions of cells with other cells and between cells and the extracellular matrix are believed to play critical roles in a wide variety of processes including, for example, modulation of the immune system, regulation of developmental processes and tumor progression and metastasis. These molecules also transduce information from the extracellular to the intracellular environment through poorly understood signalling mechanisms. The integrins represent one of the best characterized superfamilies of adhesion receptors. Integrins are glycoprotein heterodimers which contain a non-covalently associated $\alpha$ and $\beta$ subunit. Integrin subunits are transmembrane proteins which contain an extracellular domain for interacting with an extracellular matrix or cellular component, a transmembrane domain spanning the cell membrane and a cytoplasmic domain for interacting with one or more cytoskeletal components.

There are fourteen known $\alpha$ subunits and eight known $\beta$ subunits which can pair to form at least twenty different integrin molecules. Several distinct integrin $\alpha$ chains are capable of pairing with one type of $\beta$ chain to form a $\beta$ chain subfamily. Thus, for example, the $\beta_1$ subfamily includes seven members (also known as the VLA proteins: $\alpha^1\beta_1-\alpha^7\beta_1$); the $\beta_2$ subfamily includes three members (the leukocyte cell adhesion molecules or LeuCAMs: $\alpha^L\beta_2$ or LFA-1, $\alpha^M\beta_2$ or Mac-1 and $\alpha^X\beta_2$ or p150,95) and the $\beta_3$ subfamily includes two members ($a^v\beta_3$, $\alpha^{IIb}\beta_3$). In some instances, an $\alpha$ chain may pair with more than one $\beta$ chain, e.g., $\alpha^4$ can pair with $\beta_1$ or $\beta_7$.

The integrin $\alpha$ chains have in common a seven-fold repeated amino acid motif, of which the last three or four motifs include divalent cation binding sites. All known $\alpha$ chains have been divided into one of two structural groups on the basis of amino acid sequence homology and the presence or absence of two structural features (described below).

The first group of $\alpha$ chains contains a proteolytic cleavage site located in the extracellular domain, proximal to the transmembrane region. Post-translational cleavage of the $\alpha$ chain precursor yields two fragments which (with one exception) remain associated by a disulfide linkage. The smaller fragment includes a short portion of the extracellular domain, the transmembrane and the cytoplasmic domains. The larger fragment contains the major portion of the $\alpha$ chain extracellular domain. This group of post-translationally cleaved integrin $\alpha$ subunits includes $\alpha^3$, $\alpha^4$, $\alpha^5$, $\alpha^6$ (formerly called $\alpha^E$), $\alpha^v$ and $\alpha^{IIb}$, although the $\alpha^4$ molecule is a more distant member of the group since it is less similar to the other cleaved integrin $\alpha$ subunits based upon homology analysis, is cleaved near its mid-point to yield two fragments of nearly equal size and further, because the fragments are not disulfide linked (Teixido, J. et al., (1992) J. Biol. Chem. 267, 1786–1791; Rubio, M. et al., (1992) Eur. J. Immunol. 22, 1099–1102).

Members of the second group of integrin a subunits do not include the above-described proteolytic cleavage site. Moreover, the second group of a subunits is characterized by the presence of an additional region known as the "I" (inserted) domain. Homologous I domains have been identified in complement factors B and C2, von Willebrand's factor, cartilage matrix glycoprotein and collagen type VI.

The importance of integrins with respect to modulation of the immune system is illustrated by the condition, leukocyte adhesion deficiency (LAD), a disorder that is characterized by profound immunodeficiency. Individuals afflicted with LAD are unable to express the $\beta^2$ integrin subfamily (Hogg, N. (1989) Immunol. Today 10, 111–114). Thus, while it has been known for some time that integrins and other adhesion molecules function in immune system modulation, e.g., by playing a role in the adhesion of peripheral lymphocytes to endothelium and in homing to lymph nodes. However, relatively little is known about the molecules that function in the mucosal immune system, a subset of the general immune system which includes the lymphocytes which populate the gastrointestinal, genito-urinary and respiratory tracts, and the mammary glands. In particular, little is known about the molecules which function in mucosal lymphocyte homing. (see, Cepek, K. et al., (1993) J. Immunol. 150, 3459–3470 and references cited therein).

Recently, we described a novel integrin heterodimer that is expressed on intra-epithelial T lymphocytes (iIEL), i.e., the population of T lymphocytes located along the basolateral surfaces of the epithelial cells which line the mucosa, adjacent to the epithelial cell basement membrane. (Parker, C. M. et al., (1992) Proc. Natl. Acad. Sci. U.S.A. 89, 1924–1928). Originally defined by an antibody which recognizes the human mucosal lymphocyte 1 antigen (HML-1), the novel integrin is present on >90% of intestinal IEL (iIEL) and on approximately 40% of lamina propria T lymphocytes (which lie between the epithelial basement membrane and the muscularis mucosae) (Cerf-Bensussan, N. et al., (1987) Eur. J. Immunol. 17, 1279–1285). The HML-1 antigen contains a novel a chain (designated $\alpha^E$, for "epithelial associated") associated with a $\beta_7$ chain (Parker, C. M. et al., (1992) Proc. Natl. Acad. Sci. U.S.A. 89, 1924–1928). Although the HML-1 $\beta_7$ chain has been cloned (Yuan, Q. A. et al., (1990) Int. Immunol. 2, 1097–1108; Erle, D. J. et al., (1991) J. Biol. Chem. 266, 11009–11016), little is known about the primary structure of the $\alpha^E$ chain.

Cloning of the $\alpha^E$ chain has proven to be problematic because of the difficulty in obtaining an adequate number of intra-epithelial cells from which the $\alpha^E$ chain could be purified and sequenced. In addition, the relatively large length of the $\alpha^E$ gene has hampered cloning efforts because of the propensity to lose the 5' portion of relatively long genes during cDNA synthesis.

SUMMARY OF THE INVENTION

The cDNA sequence and derived amino acid sequence (Sequence I.D. Nos. 1 and 2, Genbank Accession Number L25851) for the HML-1 α chain are disclosed herein. The $\alpha^E$ chain was purified from a hairy cell leukemia spleen lysate and the N-termini of the purified protein fragments (25 kDa and 150 kDa) were sequenced to prepare degenerate oligonucleotide probes for screening a cDNA library. Surprisingly, in view of its resemblance to other integrin α subunits in overall amino acid sequence, $\alpha^E$ contains a region of 55 amino acids (referred to herein as the "X" (extra) domain or Sequence I.D. No. 4, encoded by Sequence I.D. No. 3) located N-terminal to the I domain. This region is not present in any other integrin.

The X domain contains two unique structural features: (1) an internal proteolytic cleavage site (between amino acids 160 and 161 of Sequence I.D. No. 1) followed by (2) a highly charged region of 18 consecutive amino acids (amino acids 163–180). Upon in vivo proteolytic cleavage of the $\alpha^E$ chain, two fragments are formed: a 26 kD fragment having a C-terminus which contains the 34 amino acids of the X domain N-terminus and a 150 kD fragment having an N-terminus which contains the 21 amino acids of the X domain C-terminus. The 21 amino acid portion of the X domain (referred to hereinafter as Sequence I.D. No. 5) includes the highly charged region of 18 consecutive aminoacids. The 34 amino acid portion of the X-domain N-terminus is referred to hereinafter as Sequence I.D. No. 6. These unique structural features of the X domain, coupled with the discovery that high levels of the mRNA for $\alpha^E$ (and for $\beta_7$, with which it associates to form the integrin $\alpha^E\beta_7$) are restricted to mucosal lymphocytes, suggested to us that the $\alpha^E$ subunit likely plays a unique role in the localization and/or site specific functions of intra-epithelial T-lymphocytes.

One aspect of the invention is directed to isolated peptides which inhibit the in vivo and in vitro function of the $\alpha^E$ subunit. The peptides have sequences which are related to, or derived from, the amino acid sequence of the above-described X domain (Sequence I.D. No. 4), e.g., Sequence I.D. Nos. 5, 6 and functionally equivalent peptide analogs of the foregoing peptides.

According to another aspect of the invention, a method for selecting a functionally equivalent peptide analog of Sequence I.D. No. 4 is provided. The method includes providing a peptide analog of Sequence I.D. No. 4 and determining whether the peptide analog inhibits adhesion between a human mucosal lymphocyte-1 antigen and an epithelial cell in vitro. Preferably, the peptide analogs are between about four and about twenty amino acids in length. More preferably, the peptide analogs are between about four and about ten amino acids in length. Exemplary peptide analogs are disclosed in Sequence I.D. Nos. 8 through 25, inclusive.

According to yet another aspect of the invention, a method for screening a molecular library to identify lead compounds which inhibit the in vivo activity of the integrin $\alpha^E$ chain is provided. The method includes determining whether the molecular library contains a compound which inhibits adhesion between a human mucosal lymphocyte-1 antigen and an epithelial cell in vitro. Also provided is a competitive binding assay method for identifying lead compounds which mimic the ligand binding site of the integrin $\alpha^E$ chain. The method involves determining whether the library contains a molecule which competitively inhibits the binding of the $\alpha^E$ chain (or a functionally equivalent peptide fragment or analog thereof) to an antibody which specifically recognizes the ligand binding site of the $\alpha^E$ chain.

According to another aspect of the invention, a pharmaceutical composition is provided. The composition includes a therapeutically effective amount of one or more of the above-identified isolated peptides (e.g., Sequence I.D. No. 4, a fragment or functionally equivalent peptide analog thereof) and a pharmaceutically acceptable carrier therefor, optionally, the composition further includes the $\beta_7$ chain or a portion thereof in association with the above-identified isolated peptide. Alternatively, the pharmaceutical composition includes a therapeutically effective amount of one or more isolated oligonucleotides and a pharmaceutically acceptable carrier therefor.

According to still another aspect of the invention, a support having a biologically active surface which exhibits cell attachment activity is provided. The support includes a surface to which is attached one or more of the above-disclosed peptides. Exemplary supports include a prosthesis device (e.g., a vascular graft, a percutaneous device) and an affinity matrix (e.g., for isolating the ligand(s) of the $\alpha^E$ subunit).

According to another aspect of the invention, a method for isolating a cell surface ligand of the integrin $\alpha^E$ chain is provided. The method involves coupling Sequence I.D. No. 4, or a functionally equivalent fragment or peptide analog thereof (e.g., Sequence I.D. Nos. 5–6 and 8–25), to an inert support and isolating the cell surface ligand using affinity chromatography.

According to yet another aspect of the invention, antibodies to the isolated peptides or isolated oligonucleotides are provided. The antibodies are useful for blocking a functional activity of intra-epithelial T lymphocytes, such as an in vivo functional activity (e.g., localization of the T lymphocytes) or an in vitro functional activity (e.g., adhesion of intra-epithelial T lymphocytes to an epithelial cell monolayer as determined in an adhesion assay). Accordingly, the antibodies are useful as reagents in screening assays to identify lead compounds that are present in molecularly diverse libraries or other mixtures.

According to yet another aspect of the invention, an isolated oligonucleotide is provided. The isolated oligonucleotide encodes a peptide selected from the group consisting of Sequence I.D. Nos. 4, 5, 6, 8, 9, 10, 11, 12, 13, 14, 15, 16, 17, 18, 19, 20, 21, 22, 23, 24 and 25. In a particularly preferred embodiment, the isolated oligonucleotide comprises Sequence I.D. No. 7, an oligonucleotide which encodes Sequence I.D. No. 6.

Also provided is an isolated oligonucleotide that is capable of hybridizing under stringent conditions (defined below) to the nucleotide sequence residing between about position 558 and about position 659 of Sequence I.D. No. 1. This region of the $\alpha^E$ cDNA encodes Sequence I.D. No. 6 (i.e., the relatively uncharged proteolytic cleavage fragment of the X domain). In a preferred embodiment, the isolated oligonucleotide is at least about 80% homologous with the above-recited nucleotide region of Sequence I.D. No. 1. More preferably, the isolated oligonucleotide is 100% homologous with the nucleotide sequence residing between position 558 and position 659 (referred to hereinafter as Sequence I.D. No. 7) inclusive of the $\alpha^E$ cDNA.

According to still another aspect of the invention, an antisense oligonucleotide capable of hybridizing under stringent conditions to the above-described isolated oligonucleotide is provided. The antisense oligonucleotide is capable of hybridizing to a unique fragment (defined below) of the naturally-occurring DNA or mRNA encoding the $\alpha^E$ subunit. Accordingly, delivery of an antisense oligonucleotide to intra-epithelial lymphocytes in vivo inhibits localization of the lymphocytes by base-pairing with the DNA (or RNA) encoding a unique fragment of the $\alpha^E$ nucleic acid, thereby preventing transcription (or translation) of the $\alpha^E$ subunit.

According to yet other aspects of the invention, a recombinant expression vector comprising at least one strand of the above-disclosed isolated oligonuclsotide and a cell line transfected with the recombinant expression vector are provided. Preferably, the oligonucleotide is operatively joined to at least one regulatory sequence, for example, a promoter or enhancer sequence. Suitable cell lines include mammalian cells; bacterial cells; insect cells and various yeast strains.

These and other aspects of the invention, as well as various advantages and utilities, will be more apparent with reference to the detailed description of the preferred embodiments and in the accompanying drawings.

BRIEF DESCRIPTION OF THE DRAWINGS

FIG. 3 illustrates the similarity of the $\alpha^E$ subunit with other integrin $\alpha$ subunits based upon the determination of the percent similarity of the $\alpha^E$ amino acid sequence to those of other integrin $\alpha$ subunits;

DETAILED DESCRIPTION OF THE INVENTION

I. Introduction to the Preferred Embodiments

The nucleic acid sequence and deduced amino acid sequence (Sequence I.D. Nos. 1 and 2) for a cDNA encoding the human integrin $\alpha^E$ subunit are disclosed herein. The cDNA clone was obtained by: (1) isolatingothe $\alpha^E$ subunit of the HML-1 antigen from a hairy cell leukemia spleen lysate and sequencing the N-terminus of the purified protein fragments (25 kDa and 150 kDa); (2) preparing degenerate oligonucleotide probes based upon the N-terminal amino acid sequences and screening a lambda Zap II cDNA library to obtain individual clones encoding portions of the $\alpha^E$ subunit; (3) sequencing the individual cDNA clones and preparing a composite cDNA sequence based upon overlapping sequences of individual clones; and (4) deducing the amino acid sequence for the composite cDNA. Each of these steps is described in detail in the Examples.

Two features distinguish the $\alpha^E$ subunit from previously reported alpha subunits. First, upon proteolytic cleavage, the $\alpha^E$ subunit is cleaved into a smaller (25 kDa) fragment containing Sequence I.D. No. 6 and a larger (150 kDa) fragment containing Sequence I.D. No. 5. The sequence for the smaller fragment shows sequence homology to the known integrin alpha chain amino termini, suggesting that unlike most other integrin alpha subunits which are cleaved proximal to the C-terminus or near the mid-point of the precursor polypeptide, the $\alpha^E$ precursor is cleaved proximal to the N-terminus. Second, the N-terminal sequence for the larger (150 kDa) fragment contains a region of negatively charged residues (FIG. 1) which do not share sequence homology with any known integrin a subunit sequence. As will be described in more detail below, these unique properties of the $\alpha^E$ subunit result from the presence of an additional domain (the X domain) which contains an internal proteolytic cleavage site proximal to its N-terminus.

Degenerate oligonucleotide probes having sequences based upon the N-terminal amino acid sequences of the 150 and 25 kDa fragments, were used to screen a lambda Zap II cDNA library. The composite $\alpha^E$ cDNA sequence, represented schematically in FIG. 1, was established by sequencing individual clones (depicted by thick black lines beneath the composite cDNA) and aligning the overlapping sequences. A comparison of the empirically-determined amino acid sequence for the HML-1 $\alpha^E$ subunit (FIG. 1, top line) and the amino acid sequence deduced from the cDNA sequence (FIG. 1, bottom line) demonstrated that the composite cDNA encodes the HML-1 antigen $\alpha^E$ subunit. This result was confirmed by immunoprecipitation experiments and other methods of analysis (e.g., measuring biochemical features predicted from the $\alpha^E$ cDNA, including molecular mass, proteolytic cleavage site, and the presence of N-linked glycosylation) (refer to the Examples).

Figure 1:
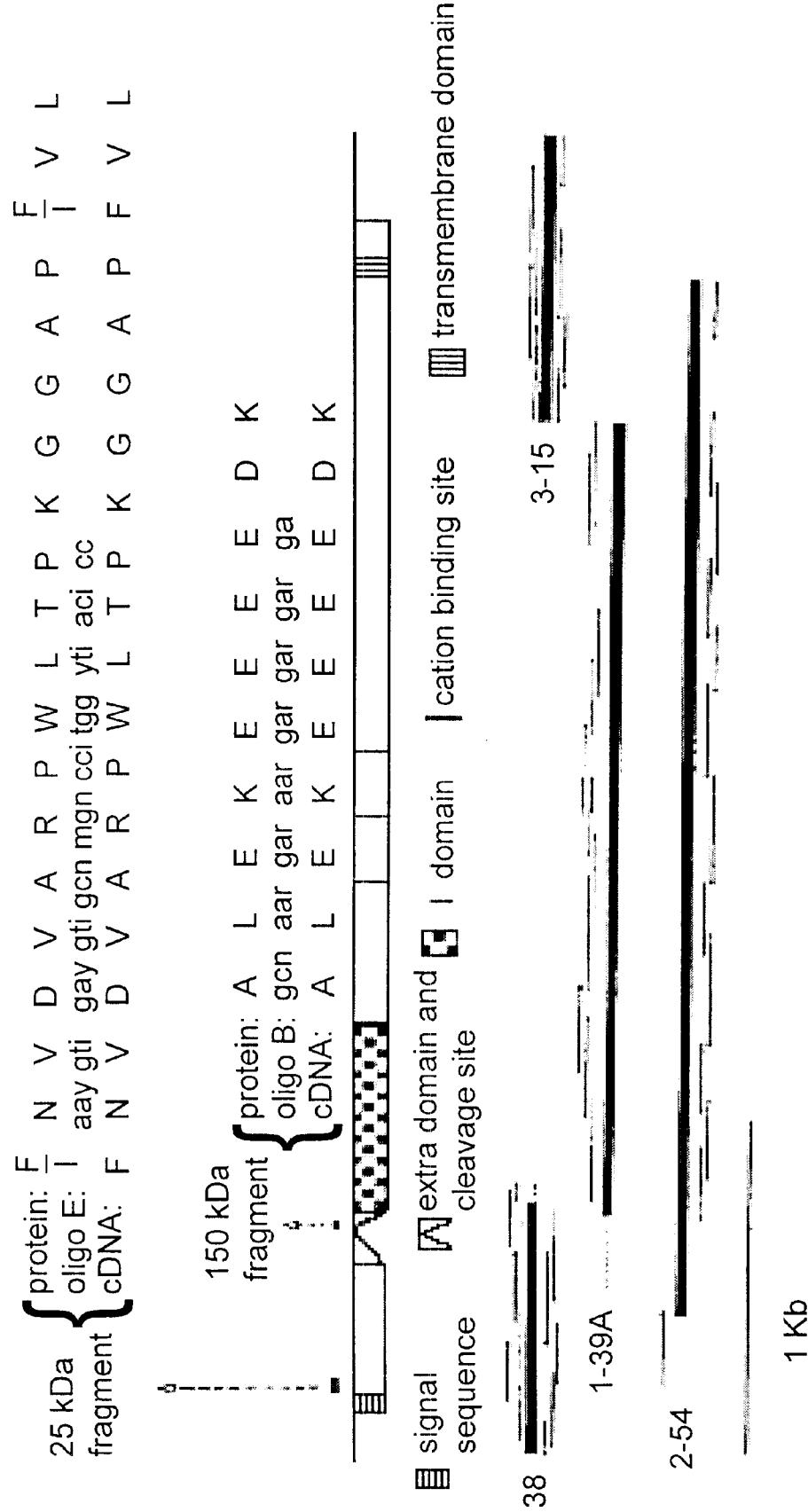
FIG. 1 schematically illustrates the composite sequence for the integrin $\alpha^E$ subunit cDNA clone and the sequencing strategy used to obtain the clone.
Figure 2:
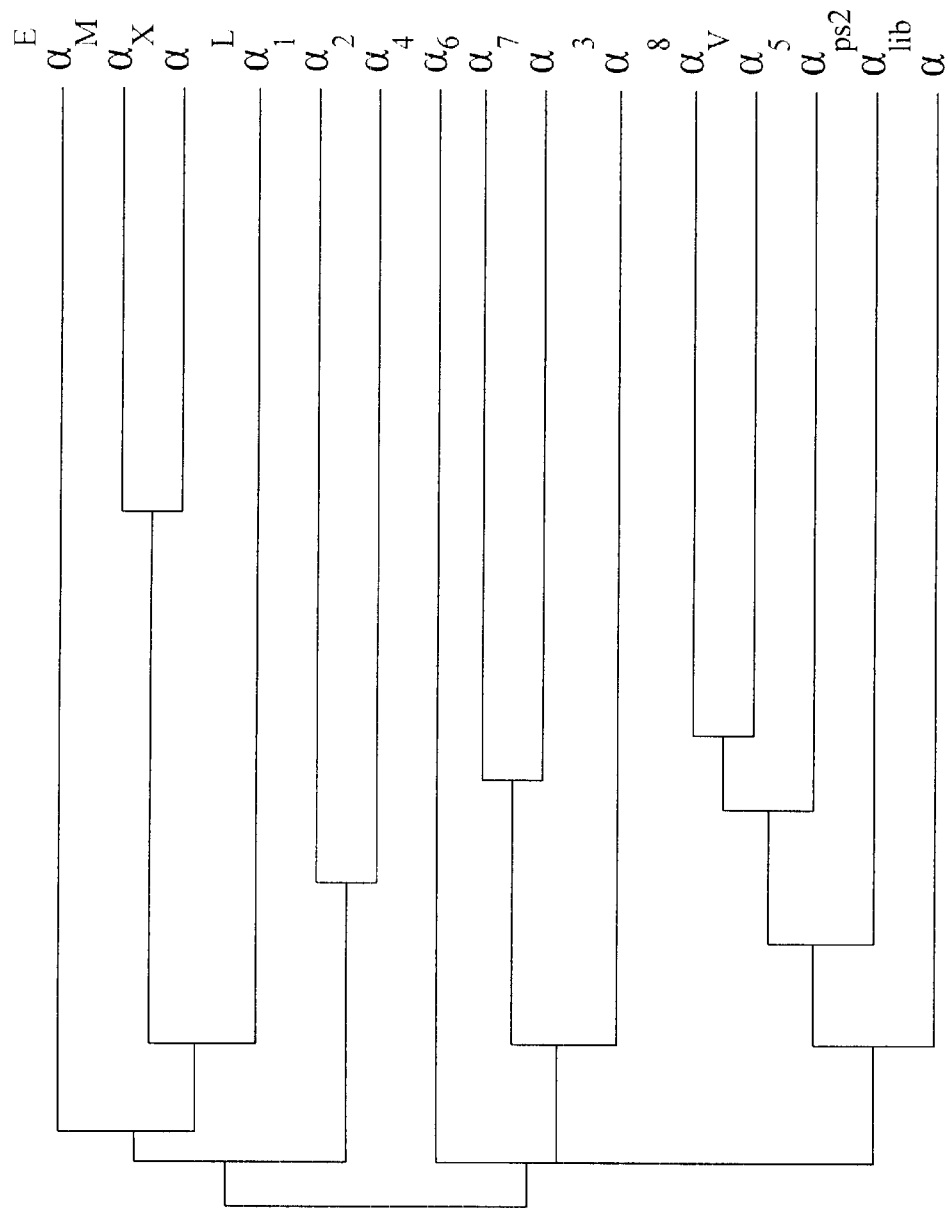
FIG. 2 illustrates the similarity of the $\alpha^E$ subunit with other integrin $\alpha$ subunits based upon generation of an integrin $\alpha$ subunit homology tree.

The nucleotide sequence of the composite cDNA and the deduced amino acid sequence are disclosed in Sequence I.D. Nos. 1 and 2, respectively. Alignment of the deduced amino acid sequence with the published sequences of other I domain-containing human integrin alpha subunits and the generation of a homology tree demonstrated substantial sequence homology between the I domain-containing subunits (FIGS. 2 and 3). However, the $\alpha^E$ subunit is a relatively distant member of the integrin I domain-containing alpha subunit family, based upon both overall sequence homology and the inclusion of the X domain (indicated in bold italics in FIG. 1).

II. The Unique X Domain

The nucleotide sequence and deduced amino acid sequence for the $\alpha^E$ subunit cDNA are shown in Sequence I.D. Nos. 1 (including the signal sequence as indicated) and 2, respectively. As used herein, the X domain refers to the unique region of 55 amino acids located proximal to the N-terminus of the I domain in the $\alpha^E$ subunit, i.e., amino acid position 127 through position 181 (encoded by nucleotide positions 558 through 722) inclusive of Sequence I.D. No. 1). Sequence I.D. No. 4 represents the deduced amino acid sequence of the X domain. Sequence I.D. No. 3 represents the oligonucleotide sequence encoding Sequence I.D. No. 4.

The X domain contains a proteolytic cleavage site, located between amino acids 160 and 161 of sequence I.D. No.1, which distinguishes the $\alpha^E$ subunit from all known integrin I domain-containing alpha subunits. Cleavage of the X domain (Sequence I.D. No. 4) yields two fragments designated Sequence I.D. Nos. 5 and 6. Sequence I.D. No. 5 contains a stretch of eighteen consecutive charged residues which are located immediately C-terminal to the cleavage site. Accordingly, the nucleic acid sequence which encodes Sequence I.D. No. 5 is identical to the coding sequence which encodes the N-terminal portion of the 150 kDa $\alpha^E$ chain.

In view of the unique primary structure of the X domain and our observation that high levels of $\alpha^E$ mRNA are found primarily in mucosal lymphocytes, we believe that the X domain is integral to the adhesion of T lymphocytes to epithelial cells in vivo. Accordingly, the invention involves producing agents which modulate that adhesion and that are useful for treating autoimmune diseases that are characterized by lymphocyte accumulation at epithelial sites (e.g., ulcerative colitis, Crohn's disease, celiac disease, sarcoidosis, psoriasis, and the late phase component of asthma). Other agents also are useful for enhancing $\alpha^E$ mediated adhesion, thereby permitting the design of more appropriate therapies for treating infectious diseases of epithelial sites (e.g., pulmonary tuberculosis, leprosy, cutaneous leishmaniosis, and parasitic or viral infections diseases of the intestinal tract) by increasing the function of mucosal intraepithelial lymphocytes or their localization to the epithelium.

According to one aspect of the invention, an isolated peptide that is capable of inhibiting the adhesion of $\alpha^E\beta_7$ to an epithelial cell in vitro also is provided. The isolated peptide has an amino acid sequence which is related to, or derived from, the amino acid sequence of the X domain (Sequence I.D. No. 4) of the $\alpha^E$ subunit. The isolated peptide is selected from the group consisting of Sequence I.D. Nos. 4, 5, 6 and functionally equivalent peptide analogs of the foregoing peptides. In a particularly preferred embodiment, the isolated peptide is Sequence I.D. No. 4, 5 or 6.

As used herein in reference to a peptide, the term "isolated" refers to an expression product of an isolated oligonucleotide; a peptide which is isolated following cleavage from a larger polypeptide; or a peptide that is synthesized, e.g., using solution and/or solid phase peptide synthesis methods as disclosed in, for example, U.S. Pat. No. 5,120,830, the entire contents of which are incorporated herein by reference.

As used herein, the term "peptide analog" refers to a peptide which shares a common structural feature with the molecule to which it is deemed to be an analog. A functionally equivalent peptide analog is a peptide analog which further shares a common functional activity (e.g., inhibiting the adhesion between an intra-epithelial T lymphocyte and an epithelial cell in vitro) with the molecule to which it is deemed an analog. Peptide analogs include unique fragments which are related to, or derived from, Sequence I.D. No. 4, polymers of Sequence I.D. No. 4, and polymers of unique fragments of Sequence I.D. No. 4. A "unique fragment" of a protein or nucleic acid sequence is a fragment which is not currently known to occur elsewhere in nature (except in allelic or allelomorphic variants). Unique fragments act as a "signature" of the gene or protein from which they are derived. A unique fragment will generally exceed 15 nucleotides or 5 amino acids. One of ordinary skill in the art can readily identify unique fragments by searching available computer databases of nucleic acid and protein sequences such as Genbank, (Los Alamos National Laboratories, USA), EMBL, or SWISS-PROT. A unique fragment is particularly useful, for example, in generating monoclonal antibodies or in screening genomic DNA or cDNA libraries.

It will be appreciated by those skilled in the art that various modifications of the foregoing peptide analogs can be made without departing from the essential nature of the invention. Accordingly, it is intended that peptides which include conservative substitutions (see, e.g., Table 2) and fusion proteins in which a peptide of the invention is coupled to a solid support (such as a polymeric bead), a carrier molecule (such as keyhole limpet hemocyanin), a toxin (such as ricin) or a reporter group (such as radiolabel or other tag), also are embraced within the teachings of the invention.

Preferably, the peptide analogs contain between about four and about twenty amino acids. More preferably, the peptide analogs contain between about four and about ten amino acids. Exemplary peptide analogs which are fragments of Sequence I.D. Nos. 4 and 5 are provided in Table 1.

TABLE 1

| Peptide Analogs (fragments of Sequence I.D. Nos. 4 and 5) | |
| --- | --- |
| EKEEEEDKEE | (Sequence I.D. No. 8) |
| KEEEEDKEEE | (Sequence I.D. No. 9) |
| EEEEDKEEEE | (Sequence I.D. No. 10) |
| EEEDKEEEED | (Sequence I.D. No. 11) |
| EEDKEEEEDE | (Sequence I.D. No. 12) |
| EDKEEEEDEE | (Sequence I.D. No. 13) |
| DKEEEEDEEE | (Sequence I.D. No. 14) |
| KEEEEDEEEE | (Sequence I.D. No. 15) |
| EEEEDEEEEE | (Sequence I.D. No. 16) |
| ALEKEEEEDK | (Sequence I.D. No. 17) |
| EEDKEEEEDEEEE | (Sequence I.D. No. 18) |
| ALEKEEEEDKEEEE | (Sequence I.D. No. 19) |
| EKEEEEDKEEEEDEE | (Sequence I.D. No. 20) |
| ALEKEEEEDKEEEEDEEEEE | (Sequence I.D. No. 21) |

As used herein, "conservative amino acid substitution" refers to an amino acid substitution which does not alter the relative charge or size characteristics of the peptide in which the amino acid substitution is made. Conservative substitutions of amino acids include substitutions made amongst amino acids within the following groups: (a) MILV; (b) FYW; (c) KRH; (d) AG; (e) ST; (f) QN; and (g) ED. Exemplary peptide analogs of Sequence I.D. No. 5 which include conservative amino acid substitutions (e.g., E for D and/or K for N) are provided in Table 2.

TABLE 2

| Peptide Analogs having Conservative Amino Acid Substitutions | |
| --- | --- |
| EKEEEEDEEEEE | (Sequence I.D. No. 22) |
| DKDDDDDDDDDD | (Sequence I.D. No. 23) |
| EDEEEEEEEEEE | (Sequence I.D. No. 24) |
| ENEEEEDNEEEED | (Sequence I.D. No. 25) |

As used herein, the term "functionally equivalent peptide analog" refers to a peptide analog that is capable of inhibiting the binding of an intra-epithelial T lymphocyte to an epithelial cell in vitro. An in vitro adhesion assay (see, e.g., the adhesion assay provided in the Examples) is used as a screening assay to measure the ability of a molecule, e.g., a peptide analog, to inhibit $\alpha^E\beta_7$-mediated adhesion between an intra-epithelial T lymphocyte and an epithelial monolayer in culture and is predictive of the ability of a molecule to inhibit the functional activity of the novel $\alpha^E\beta_7$ subunit in vivo. For example, a "functionally equivalent peptide analog" of Sequence I.D. No. 4 includes fragments of Sequence I.D. No. 4, as well as peptide analogs of Sequence I.D. Nos. 4–6 which contain conservative amino acid substitutions, provided that the peptide fragments and analogs are capable of inhibiting adhesion of a human intra-epithelial lymphocyte to an epithelial cell.

According to yet another aspect of the invention, a method for selecting a functionally equivalent peptide analog of Sequence I.D. No. 4 is provided. The method involves providing a peptide analog of Sequence I.D. No. 4 and determining whether the peptide analog inhibits adhesion between a human mucosal lymphocyte-1 antigen and an epithelial cell in vitro. In a particularly preferred embodiment, the functionally equivalent peptide analogs are fragments of Sequence I.D. No. 4 containing between about four and about twelve amino acids and having about the same isoelectric point as Sequence I.D. No. 5 (see, e.g., Table 1, above).

According to yet another aspect of the invention, a method is provided for screening a molecular library to identify pharmaceutical lead molecules, i.e., molecules which inhibit the adhesion between an intra-epithelial T lymphocyte and an epithelial cell in vitro. A molecular library refers to a collection of structurally-diverse molecules and includes both recombinantly-produced and chemically-synthesized libraries. As used herein, "library molecule" refers to a molecule that is present in the molecular library. Accordingly, screening refers to the process by which library molecules are tested for the ability to inhibit the adhesion between an intra-epithelial T lymphocyte and an epithelial cell or the ligand binding activity of the $\alpha^E \beta_7$ subunit. For example, the ability of a molecule to inhibit the binding of a mucosal T-lymphocyte (or the $\alpha^E \beta_7$ subunit) to an epithelial cell in vitro can be used as a screening assay to identify lead compounds. Thus, a particularly preferred screening method involves determining whether the library molecule (or peptide analog) inhibits adhesion between a human mucosal lymphocyte-1 antigen and an epithelial cell in culture. Such adhesion assays are well known in the art and are illustrated by the assay provided in the Examples.

Alternatively, antibodies which specifically recognize the ligand binding site of the $\alpha^E \beta_7$ integrin (i.e., that portion of the subunit which-binds to an epithelial cell) can be used to screen combinatorial libraries (e.g., by contacting the library with the antibody and determining whether the library contains a molecule which competitively inhibits binding of the antibody to a peptide known to contain the ligand binding site). Such competitive binding assays also can be used to assess the relative affinity of the library molecule for its cognate (e.g., a ligand present on an epithelial cell). Antibodies to the ligand binding site also can be used to purify the integrin heterodimer or its subunits which bind to ligand expressed on the epithelial cell.

According to yet another aspect of the invention, methods and compositions for modulating the functional activity of the ORB, integrin in vivo are provided. One method involves administering a pharmaceutical composition containing a therapeutically effective amount of the isolated peptides and/or oligonucleotides of the invention. In general, the therapeutically effective amount is between about 1 ug and about 100 mg/kg. The preferred amount can be determined by one of ordinary skill in the art in accordance with standard practice for determining optimum dosage levels of the agent. The peptides (and/or oligonucleotides) are formulated into a pharmaceutical composition by combination with an appropriate pharmaceutically acceptable carrier. For example, the peptides may be used in the form of their pharmaceutically acceptable salts, or may be used alone or in appropriate association, as well as in combination with other pharmaceutically active compounds. The peptides may be formulated into preparations in solid, semisolid, liquid or gaseous form such as tablets, capsules, powders, granules, ointments, solutions, suppositories, and injections, in usual ways for oral, parenteral, or surgical administration. Exemplary pharmaceutically acceptable carriers are described in U.S. Pat. No. 5,211,657, the entire contents of which patent are incorporated herein by reference.

The invention also includes locally administering the composition ag an implant or any part of it either alone or bound to a synthetic material, such as a vascular prosthesis. Accordingly, a support (e.g., nitrocellulose, polyester, polyvinyl, polystyrene or a ceramic) having a biologically active surface which exhibits cell attachment activity also is provided. As used herein, a "biologically active surface which exhibits cell attachment activity" refers to a support to which is attached at least one of the above-identified isolated peptides. Attachment of the peptides confers upon the support surface the ability to attach cells, and in particular, the ability to attach epithelial cells.

Methods for preparing a biologically active surface by coupling a peptide to an inert surface are disclosed in U.S. Pat. No. 5,211,657, the contents of which have been incorporated herein by reference. The peptides are coupled to plastic surfaces for in vitro use (e.g., for cell culture in which it is desirable to attach cells to a culture vesicle), to a prosthesis such as a vascular prosthesis or other artificial organ to make the synthetic materials more biocompatible and to allow the cells to adhere and grow or to an affinity matrix. Alternatively, the peptides are incorporated into a polymer during the polymerization process, rather than attached to the surface of a previously formed inert support.

According to yet another aspect of the invention, a method for isolating a ligand for the integrin $\alpha^E \beta_7$ subunit from detergent extracts of cells or cell membranes is provided. The method includes (1) specifically adsorbing the ligand to an affinity matrix having Sequence I.D. No. 4 or a functionally equivalent peptide analog thereof coupled to the matrix to form a ligand-adsorbed affinity matrix, and (2) adding to the ligand-adsorbed affinity matrix a plurality of peptides selected from the group consisting of Sequence I.D. No. 4 and a functionally equivalent peptide analog of Sequence I.D. No. 5 to specifically elute the ligand from the affinity matrix. In a particularly preferred embodiment, the peptide coupled to the matrix is Sequence I.D. No. 4, 5 or 6.

As used herein, "affinity matrix" refers to an inert support to which molecules can be covalently attached in a manner such that the ligand binding portion of the molecule is exposed. The methods for coupling a molecule (e.g., a peptide) to an affinity matrix are determined by the nature of the functional groups present on the molecule and on the matrix (e.g., amine groups, carboxyl groups). The peptide can be derivatized (according to standard procedures known in the art) to include additional functional groups to facilitate the coupling of the peptide to the matrix in a desired orientation. Typically, matrices are sold in an activated form for coupling to a specified class of functional groups. In such instances, instructions for coupling a molecule to the matrix are provided by the matrix manufacturer. Numerous types of coupling methods to a variety of inert supports are well known to those of ordinary skill in the art.

According to another aspect of the invention, an antibody specific for the $\alpha^E$ subunit is provided. The antibodies are raised against the above-identified isolated peptides and/or fusion peptides using well known immunization techniques (see, e.g., the Examples: generation of an antibody to the synthetic C-terminal peptide predicted from the $\alpha^E$ cDNA). Preferably, the antibody specifically recognizes an antigen selected from the group consisting of the X domain (Sequence I.D. No. 4) and fragments or equivalents of the X domain. In a particularly preferred embodiment, the peptides are selected from the group consisting of Sequence I.D. Nos. 4–6 and 8–21. The antibodies are useful in screening assays for identifying pharmaceutical lead compounds which inhibit the adhesion of an intra-epithelial T lymphocyte to an epithelial cell.

The antibodies also are useful in vivo for blocking cell adhesion and localization of intra-epithelial T lymphocytes and for example, targeting a toxin (e.g., ricin) or detectable agent (e.g., a radiolabel, a fluorescent label, an enzyme label) to cells (e.g., intra-epithelial lymphocytes) containing the $\alpha^E$ subunit. Methods for coupling such toxins and/or agents to proteins and/or antibodies for in vivo and in vitro applications are disclosed in, for example, Killen and Lindstrom (1984), "Specific killing of lymphocytes that cause experimental Autoimmune Myestenia Gravis by toxin-acetylcholine receptor conjugates", J. Immun. 133:1335; Jansen, F. K., et al. (1982), "Immunotoxins: Hybrid molecules combining high specificity and potent cytotoxicity", Immunolog. Rev. 62:185–216, the entire contents of which references are incorporated herein by reference. See also U.S. Pat. Nos. 3,652,761; 4,478,946 and 4,554,088, the entire contents of which patents are incorporated herein by reference.

The invention also provides isolated oligonucleotides (e.g., Sequence I.D. No. 3) that encode the X domain (Sequence I.D. No. 4), its proteolytic fragments (Sequence I.D. Nos. 5 and 6) and the above-described functionally equivalent peptide analogs of the foregoing amino acid sequences (Sequence I.D. Nos. 8–25). As used herein, the term "isolated" in reference to an oligonucleotide, means an RNA or DNA polymer, portion of genomic nucleic acid, cDNA or synthetic nucleic acid which, by virtue of its origin or manipulation: (a) is not associated with all of a nucleic acid with which it is associated in nature (e.g., is present in a host cell as a portion of an expression vector); or (b) is linked to a nucleic acid or other chemical moiety other than that to which it is linked in nature; or (c) does not occur in nature. By "isolated" it is further meant a nucleic acid sequence: (i) amplified in vitro by, for example, the polymerase chain reaction (PCR); (ii) synthesized by, for example, chemical synthesis; (iii) recombinantly produced by cloning; or (iv) purified from a more complex molecule or from a mixture of molecules, such as by cleavage and size fractionation. Due to the degeneracy of the genetic code, many different oligonucleotide sequences can be identified which encode Sequence I.D. Nos. 4–6 and 8–25. Accordingly, the invention embraces oligonucleotides which encode the X domain (as well as its fragments) but which have nucleotide sequences which differ from the sequences of the naturally-occurring $\alpha^E$ gene or from the cDNA disclosed in Sequence I.D. No. 1.

In addition to the foregoing oligonucleotides, the invention also provides an isolated oligonucleotide that is capable of hybridizing under stringent conditions to the nucleotide sequence residing between position 558 and position 722 inclusive of Sequence I.D. No. 1 (i.e., the region of the $\alpha^E$ cDNA which encodes the X domain (Sequence I.D. No. 4)). As used herein, the phrase "hybridizing under stringent conditions" is a term of art which refers to the conditions of temperature and buffer concentration which will permit hybridization of a particular oligonucleotide or nucleic acid to its complementary sequence and not to non-complementary sequences. The exact conditions which constitute "stringent" conditions, depend upon the length of the nucleic acid sequence and the frequency of occurrence of subsets of that sequence within other non-identical sequences. By varying hybridization conditions from a level of stringency at which no hybridization conditions occurs to a level at which hybridization is first observed, one of ordinary skill in the art can, without undue experimentation, determine conditions which will allow a given sequence to hybridize only with identical sequences. Suitable ranges of such stringency conditions are described in Krause, M. H. and S. A. Aaronson, Methods in Enzymology, 200:546–556 (1991). Stringent hybridization conditions, depending upon the length and commonality of a sequence, may include hybridization conditions of from 30 to 60 degrees C. and from 5 × to 0.1×SSC. Highly stringent hybridization conditions may include hybridization at 45 degree C. and 0.1 SSC. Less than stringent conditions are employed to isolate nucleic acid sequences which are substantially similar, allelic or homologous to any given sequence. In a particularly preferred embodiment, the isolated oligonucleotide is 100% homologous with the nucleotide sequence residing between position 558 and position 722 inclusive of Sequence I.D. No. 1. Exemplary high stringency hybridization conditions are provided in the Examples.

Alternatively, the isolated oligonucleotide is capable of hybridizing under stringent conditions to a unique fragment of the nucleotide sequence residing between positions 558 and 722 of Sequence I.D. No.1. As used herein, the phrase "unique fragment" refers to a nucleic acid sequence having less than 25% sequence homology with previously identified nucleic acid sequences. More preferably, the unique fragments have less than 10% sequence homology with known nucleic acid sequences. Such unique fragments can be identified by searching the Genbank, PIR and/or Swiss-Prot data bases (e.g., release date Jan. 20, 1994) using the Eugene program available through the Harvard Molecular Biology Core Research Resource, Cambridge, Mass. For example, using the entire X domain, several classes of intranuclear DNA binding proteins and intracytoplasmic proteins were identified as having some degree of sequence homology with the X domain. These proteins included neurofilament triplet M protein, nucleolin, troponin T, alphaglobulin type B precursor (tandem 1), legumin B LegJ precursor, major centromere autoantigen CENP-B, calreticulin precursor (clone 3) and non-histone chromosomal protein HMG-1. These proteins had, at most, about 50% sequence homology over 35 amino acids or about 35% sequence homology over 54 amino acids. The regions of sequence homology were located in the negatively charged, glutamate-rich region, with less than 20% sequence homology observed for the relatively uncharged portion of the X domain (Sequence I.D. No. 6).

In view of the many DNA binding proteins which contain highly negatively charged regions for binding to DNA, it is likely that the observed sequence homology between the highly charged region of the X domain and the above-mentioned intranuclear DNA binding proteins is coincidental and does not reflect a similar functional activity (e.g., the ability to bind to a ligand expressed on an epithelial cell) between the X domain and these DNA binding proteins. Hence, Sequence I.D. Nos. 6 and 7 are deemed to be unique fragments of the $\alpha^E$ subunit amino acid and nucleotide sequences, respectively. Accordingly, in a particularly preferred embodiment, the isolated oligonucleotide is Sequence I.D. No. 7 (the sequence corresponding to nucleotides 558 through 659 inclusive of the $\alpha^E$ cDNA). The unique fragments are useful, for example, as probes and primers in nucleic acid hybridization assays and in amplification reactions, respectively.

For applications directed to the use of an isolated oligonucleotide for regulating transcription and/or translation of the $\alpha^E$ subunit, the preferred oligonucleotide is an antisense oligonucleotide between about 10 and about 100 nucleotides in length. The antisense oligonucleotide is capable of hybridizing under high stringency conditions to the above-described unique fragments of Sequence I.D. No. 1. As used herein, "antisense oligonucleotide" refers to an oligonucleotide (DNA and/or RNA) that is capable of hybridizing to the naturally-occurring DNA or mRNA encoding the novel $\alpha^E$ subunit of human integrin. In a preferred embodiment, the antisense oligonucleotide is capable of hybridizing in vivo to the nucleotide sequence residing between positions 558 and 659 inclusive of Sequence I.D. No. 1 or its transcription product. Base-pairing of the antisense oligonucleotide with the DNA (or RNA) encoding the uncharged region of the $\alpha^E$ subunit in vivo, prevents localization of intra-epithelial lymphocytes by preventing transcription (or translation) of the $\alpha^E$ subunit.

Methods for expressing the above-identified oligonucleotides in a suitable expression system including a host cell are well known to those of ordinary skill in the art (see, e.g., Sambrook, et al., *Molecular Cloning, A Laboratory Manual*, 2d ed., Cold Spring Harbor Laboratory Press, Plainview, N.Y. (1989)). The term "host. cell" refers to a prokaryotic or eukaryotic cell which, together with a recombinant vector, comprises an expression system. The term host cell also embraces a host cell in which the vector or isolated oligonucleotide has integrated into the host cell nucleic acid. In a preferred embodiment, the expression vector includes at least one strand of the above-disclosed isolated oligonucleotide. Preferably, the oligonucleotide is operatively joined to at least one regulatory sequence, e.g., a promoter sequence, an enhancer sequence. A coding sequence (e.g., the isolated oligonucleotide) and a regulatory sequence are said to be operably joined when they are linked in such a way as to place expression of the coding sequence under the influence or control of the regulatory sequence.

Suitable cell lines include mammalian cells (e.g., Chinese hamster ovary cells (CHO), monkey COS-1 cell); bacterial cells (e.g., *E. coli, B. subtilis* and Pseudomonas strains); insect cells (e.g., SF9) and various yeast strains. Exemplary procedures for obtaining expression of a foreign gene in the above-identified cell lines are disclosed in U.S. Pat. No. 5,211,657, the entire contents of which are incorporated herein by reference.

EXAMPLES

The methodology for construction, isolation and characterization of the integrin $\alpha^E$ cDNA clone of the present invention is described in detail in Example 1. An exemplary method for identifying peptide analogs which inhibit $\alpha^E \beta_7$-mediated adhesion between intra-epithelial T lymphocytes and epithelial cells is described in detail in Example 2. All references recited in this application are incorporated in their entirety herein by reference.

Example 1

Cloning and Characterizing the $\alpha^E$ Subunit cDNA
Materials and Methods

Purification and sequencing of the HML-1 α chain. Purification of the $\alpha^E \beta_7$ complex was performed by immunoaffinity column chromatography from a human hairy cell leukemia spleen lysate using the Ber-ACT8 monoclonal antibody, as previously described (Parker, C. M. et al., (1992) Proc. Natl. Acad. Sci. U.S.A. 89, 1924–1928). The HML-1 antigen was then resolved by SDS-PAGE under non-reducing conditions (Hochstenback, F. et al., (1988) J. Exp. Med. 168, 761–776), and the region of the gel containing the larger 175 kDa subunit was excised and equilibrated in reducing buffer: 125 mM tris-Cl, 0.1% (w/v) SDS, 5% (v/v) 2-mercaptoethanol, and 10% (v/v) glycerol. The two resulting $\alpha^E$ fragments of 150 kDa and 25 kDa were then separated on a second SDS/PAGE gel under reducing conditions and electroblotted to a poly(vinylidene difluoride) membrane (Problott: Applied Biosystems) in 10 mM CAPS pH 11, 10% Methanol. The HML-1 α subunit 150 kDa and 25 kDa fragments were visualized by Coomassie blue staining and sequenced using an Applied Biosystems model 470A gas-phase sequencer equipped with a model 120A phenylthiohydantoin amino-acid sequencer (Harvard Microsequencing Facility, Cambridge, Mass.). Approximately 9 pMol of the 150 kDa fragment and 19 pMol of the 25 kDa fragment were analyzed.

Preparation of cDNA library. RNA was prepared using the urea/LiCl method (Auffray, C. et al., (1980) Eur. J. Biochem 107, 303–314) from $3 \times 10^8$ IEL that had been cultured for 5 days with 2 ng/ml TGF-β1 (gift of Celtrix, Palo Alto, Calif.). Poly (A) RNA was selected and cDNA was synthesized from this RNA in the presence of methylmercuric hydroxide using both random oligonucleotides as well as poly d(T) as primers. The cDNA was size fractionated to selectively remove low molecular weight species (under 500 bp) and the two types of cDNA were mixed, methylated, and ligated into the lambda zapII vector (Stratagene, La Jolla, Calif.). The library contained inserts ranging from 0.6–5 kb, with $1.4–10^6$ independent clones (Clontech laboratories Inc., Palo Alto, Calif.).

Isolation of cDNA clones. Based upon the determined N-terminal amino acid sequences of the $\alpha^E$ 150 kDa and 25 kDa fragments, two degenerate oligonucleotide probes were generated (FIG. 1). Inosine residues were used to reduce the degree of degeneracy. The amplified cDNA library was screened by plaque filter hybridization in 6×SSC, 0.5% (w/v) SDS, 50 mM HEPES, pH 7, 5×Denhardt's solution, and 1 mM EDTA, with each of these $^{32}P$ end-labelled oligonucletides using standard techniques (Sambrook, J. et al., (1989) Molecular Cloning: A Laboratory Manual, 2nd Ed., Cold Spring Harbor Laboratory Press). Filters were washed at low stringency at room temperature in 2×SSC, 0.5% (w/v) SDS. The filters were then washed under stringent conditions, at 37° C. for 10 minutes (oligonucleotide E: 2×SSC, 0.5% (w/v) SDS; oligonucleotide B: 3 M tetramethylammonium chloride (Aldrich), 2 mM EDTA, 50 mM tris-Cl pH 8). Plaques which hybridized with both oligonucleotides were purified. Each subsequent screening was performed with cDNA restriction fragments isolated from clones identified in earlier screenings. These restriction fragments were labelled using random-priming hexamers, and the filters were hybridized under stringent conditions in 4.8×SSC, 50 mM HEPES, pH 7, 0.5% (w/v) SDS, 5X Denhardt's solution, 50% formamide, and 200 ug/ml sheared denatured salmon sperm DNA (Sigma). Filters were stringently washed in 0.2% SSC, 0.1% SDS, at 37° C. for 1 hour. Positive clones were subcloned in the Bluescript SK(−) plasmid (Stratagene), with the helper phage R407, using an in vivo excision protocol (Short, J. M. et al., (1988) Nucleic Acids Res. 16, 7583–7600), and restriction mapped using standard procedures (Sambrook, J. et al., (1989) Molecular Cloning: A Laboratory Manual, 2nd Ed., Cold Spring Harbor Laboratory Press).

Nucleotide sequencing. The ends of inserts of positive clones were sequenced using the T3 and T7 primer regions from the Bluescript SK(−) vector. Additionally, a series of deletion clones were generated from selected inserts using Exonuclease III (Erase-a-base kit, Promega) in order to sequence their interior regions. Sequencing reactions were performed using the double-standard dideoxy-termination method (Sequenase kit, USBiochem) and the sequence was analyzed by computer using DNAStar, DNA Strider, and the Genetics Computer Group software package (Madison, Wis.) on the Molecular Biology Computer Research Resource Facility (Dana Farber Cancer Institute, Boston, Mass.). Many clones isolated had extraneous sequence attached to one or both ends (FIG. 1), which was not present in any other clone. However, it was possible to recognize the $\alpha^E$ encoding sequence based on overlaps with other previously identified clones, i.e., those clones identified in a prior round of screening. For example, clone 38 (identified in a first round of screening), was used to identify clone 1-39A. A 3' fragment of clone 1-39A then was used to rescreen the library and identify clone 2-54. Thereafter, a 3' fragment of clone 2-54 was used to identify clone 3-15.

Monoclonal Antibodies and Cell Lines

Previously described mAb used were HML-1 (mouse anti-human $\alpha^E\beta_7$ IgG2a) (Cerf-Bensussan, N. et al., (1987) Eur. J. Immunol. 17, 1279–1285), Ber-ACT8 (mouse anti-human $\alpha^E\beta_7$, IgG1) (Kruschwitz, M. et al., (1991) J. Clin. Path 44, 636–645), OKT3 (mouse anti-human CD3, IgG2a, available from American Type Culture Collection (ATCC), Bethesda, Md.), OKT4 (mouse anti-human CD4, IgG2b, ATCC), OKT8 (mouse anti-human CD8*, ATCC), 64.1 (mouse anti-human CD3) (Hansen, J. A. et al., (1984) in Leukocyte typing: Human Leukocyte Differentiation Antigens detected by Monoclonal antibodies, 195–212), SPV-T3b (mouse anti-human CD3, IgG2a) (Spits, H. et al., (1983) Hybridoma 2, 423–437), 3C10 (mouse anti-human CD14, IgG2b) (Van Voorhis, W. C. et al., (1983) J. Exp. Med. 158, 126–145), HB12B (mouse-anti human CD19, IgG1) (Kansas, G. S. et al., (1991) J. Immunol. 147, 4094–4102), B1 (mouse anti-human CD20, IgG2a) (Stashenko, P. et al., (1980) J. Immunol. 125, 1678–1685) and the anti-$\beta_7$ C-terminal peptide (amino acids 736–755) antiserum (Parker, C. M. et al., (1992) Proc. Natl. Acad. Sci. U.S.A. 89, 1924–1928).

To produce an anti-$\alpha^E$ C-terminal peptide serum, a peptide was synthesized corresponding to residues 1137–1161 deduced to lie in the $\alpha^E$ cytoplasmic tail, with an added cysteine residue at the amino terminus of the peptide to permit coupling to carrier protein. The peptide was conjugated to keyhole limpet hemocyanin (Pierce, Rockford, Ill.), using the heterobifunctional cross linking agent, m-Maleimidobenzoyl-N-hydroxysulfosuccinimide (Pierce), according to the manufacturer's instructions. Rabbit antisera were generated by immunization with the conjugated $\alpha^E$1137–1161 peptide using standard protocols (Harlow, E. et al., (1988) Antibodies: A Laboratory Manual, Cold Spring Harbor Laboratory Press).

To produce an anti-$\alpha^E$ X domain (charged fragment) peptide serum, a peptide was synthesized containing ALEKEEEDKEEEEDEEEEC (SEQ ID NO:26) and antibodies were generated using the same protocol as described above for generating peptides to the $\alpha^E$ C-terminal peptide. The antiserum produced thereby was capable of immunoprecipitating the $\alpha^E\beta_7$ heterodimer.

iIEL lines were derived and cultured as previously described (Cepek, K. L. et al., (1993) J. Immunol. 150, 3459–3470). Cultured tumor lines (PEER, MOLT 4, MOLT 13, MOLT 17, HPB-ALL, HUT 78, JY', VA2, RD, HeLa, A431) were maintained in RPMI-1640 (GIBCO, Grand Island, N.Y.) containing 10% fetal bovine serum (Hyclone, Logan, Utah.). The epithelial cell line 16E6. A5 was maintained in DFCI-1 medium (Cepek, K. L. et al., (1993) J. Immunol. 150, 3459–3470).

Leukocyte concentrates produced as a by-product from plateletphoresis of randomly selected healthy donors were used as a starting material to isolate fresh peripheral blood monocytes and T cells. Peripheral blood mononuclear cells (PBMC) were separated by density gradient centrifugation (Ficoll-Plaque, Pharmacia LKB, Piscataway, N.J.) and monocytes were isolated by adherence to polystyrene tissue culture flasks (Porcelli, S. et al., (1992) Nature 360, 593–597) and used to prepare RNA (see below). A fraction of the adherent cells in a separate flask were detached by incubation at 37° C. in PBS/0.5 mM EDTA, and analyzed by flow cytometry using the FACScan flow cytometer (Beckton Dickinson, Mountain View, Calif.) to reveal 91% CD14+, 2% CD19/20+, and <1% CD3+ cells. T lymphocytes were isolated from the non-adherent PBMC using an anti-CD3 antibody, 64.1, and positive selection by magnetic bead separation (Dynabeads M-450, Dynal A. S., Oslo, Norway) according to the manufacturer's instructions. To isolate B lymphocytes, surgically removed fresh tonsils were teased into fragments with forceps and forced through a wire mesh. The resulting cell suspension was subjected to density gradient centrifugation (Ficoll-Paque) to obtain mononuclear cells. Tonsillar B cells were further purified by depleting T lymphocytes with mAbs recognizing CD3 (64.1), CD4 (OKT4) and CD8 (OKT8) and negative selection by magnetic bead selection. An aliquot of the negatively selected population was analyzed by flow cytometry: 97% were positive with anti-CD19+anti-CD20 mAbs (HB-12b and B1) and 1.3% were positive with anti-CD3 (SPV-T3b).

Neutrophils were purified from peripheral blood as previously described (Neuman, E. et al., (1992) J. Immunol. 148, 3520–3527). Differential analysis was performed using Wright's/Giemsa stained cytospin preparations, and revealed 92% neutrophils, with 8% eosinophils.

Immunoprecipitations

TGF-$\beta$1 treated cultured iIEL ($35\times10^6$ cells) were surface radioiodinated with 1 mCi of $Na^{125}I$ using lactoperoxidase, lysed in 1 ml of 0.5% Triton-X100, 8 mM iodoacetamide, 10 mM phenylmethylsulfonyl fluoride in TBS (50 mM tris-Cl, pH 7.6, 140 mM NaCl), and precleared with 4 ul normal rabbit serum, followed by 200 ul of Staphylococcal A Cowan I. Following centrifugation, supernatant containing $3\times10^6$ cell equivalents was used for each specific immunoprecipitation, using 5 ul of antiserum, or 0.1 ul of HML-1 mAb ascites, as previously described (Hochstenbach, F. et al., (1988) J. Exp. Med. 168, 761–776). Following a 1 hour incubation at 4° C., the supernatant was incubated for 1 hour with 75 ul protein A-SEPHAROSE® (crosslinked organose beads) (10%, w/v, in TBS). The immune complexes were washed five times in wash buffer (0.1% v/v Triton-X100/TBS), eluted with sample buffer (5% glycerol, 1.5% (w/v) SDS, 0.2% (w/v) bromophenol blue, 188 mM tris-Cl pH 8.8) and resolved on a 7% denaturing polyacrylamide gel under non-reducing conditions (Hochstenbach, F. et al., (1988) J. Exp. Med. 168, 761–776).

In the reprecipitation experiment, $7\times10^7$ cultured iIEL were radioiodinated with 2.5 mCi, lysed and precleared as above. A specific immunoprecipitation was performed with the entire lysate, using 2 ul of HML-1 mAb ascites, followed by 300 ul of protein A-SEPHAROSE® (crosslinked organose beads). After 5 washes in wash buffer, $\alpha^E\beta_7$ was eluted from the matrix by heating in a boiling water bath for 5 minutes in 150 ul of 1% (w/v) SDS. Following brief centrifugation, the supernatant was collected and treated with 150 ul precleared fetal calf serum for 30 minutes. Four ml of 2% (v/v) Triton-X100/TBS were added, and the supernatant incubated overnight at 4° C. Equal aliquots of 600 ul were then precleared and immunoprecipitated with the anti-$\alpha^E\beta_7$ mAb HML-1 (0.1 ul), the anti-$\alpha^E$1136–1160 C-terminal peptide serum (10 ul), followed by protein A-SEPHAROSE® (crosslinked organose beads) (75 ul). Immune complexes were washed and the reprecipitated proteins eluted, and resolved by SDS-PAGE under non-reducing conditions, as previously described (Hochstenbach, F. et al., (1988) J. Exp. Med. 168, 761–776).

Northern Blot Analysis. RNA was prepared from cell lines and leukocyte fractions using guanidium isothiocyanate lysis, followed by acid-phenol/chloroform extraction (Chomczynski, P. et al., (1987) Anal. Biochem 162, 156–159). Poly(A) RNA was isolated from total RNA using standard techniques (Sambrook, J. et al., (1989) Molecular Cloning: A Laboratory Manual, 2nd Ed., Cold Spring Harbor Laboratory Press). RNA was resolved on 1.2% agarose-formaldehyde gels and transferred to nylon membranes (Hybond N: Amersham). Commercially available Northern blots (Clontech) were used to analyze human tissue RNA. Blots were hybridized at 42° C. in 5×SSPE (Sambrook, J. et al., (1989) Molecular Cloning: A Laboratory Manual, 2nd Ed., Cold Spring Harbor Laboratory Press), 10×Denhardt's solution, 50% (v/v) formamide, 2% (w/v) SDS, and 100 ug/ml salmon sperm DNA. Blots were washed in 0.1×SSC, 0.1% (w/v) SDS, at 50° C., for one hour.

The probes used to analyze the Northern blots included the $\alpha^E$ cDNA probe which consisted of two restriction fragments in approximately equimolar amounts and spanning approximately ⅓ of the deduced coding sequence, extending from nucleotide 1915–2394 (1-39A Apa I-BamH I) and 2394–3084 (1-39A BamH I-EcoR I). The $\beta_7$ probe extended from nucleotide 47-2801 of the published sequence (Yuan, Q. A. et al., (1990) Int. Immunol. 2, 1097–1108). The glyceraldehyde 3-phosphate dehydrogenase (GAP) probe (Clontech) extended from nucleotide 71-1053 of the published sequence (Arcari, P. et al., (1984) Nucleic Acids Res. 12, 9179–9189).

Results

Purification and N-terminal Amino Acid Sequence of the $\alpha^E$ Chain:

To determine the primary amino acid sequence of the $\alpha^E$ protein, the HML-1 ($\alpha^E\beta_7$) complex was purified from a hairy cell leukemia spleen lysate by immunoaffinity column chromatography, followed by two stages of SDS-PAGE (see Materials and Methods). The $\alpha^E$ subunit resolved under reducing conditions into 150 kDa and 25 kDA fragments. A sequence of 20 amino acids was determined from the N-terminus of the 25 kDa fragment (FIG. 1). Surprisingly, it was this sequence, not that from the 150 kDa fragment, which bore homology to known integrin α chain amino termini. This suggested that $\alpha^E$ was cleaved towards the N-terminal portion of the precursor polypeptide, unlike other integrins which are cleaved proximal to the C-terminus or near the midpoint. The N-terminal sequence from the 150 kDa fragment showed a preponderance of negatively charged residues (FIG. 1), with no significant homology with previously identified integrin α chains.

Cloning of a cDNA Encoding $\alpha^E$:

To clone a cDNA encoding $\alpha^E$, a lambda Zap II cDNA library was synthesized from TGF-beta1 treated iIEL mRNA using both oligo d(T) and random priming. Based on the amino acid sequence obtained from the 150 and 25 kDa fragments, corresponding degenerate oligonucleotides were synthesized, one from each, and were used to screen the library (FIG. 1). Analysis of 420,000 phage plaques resulted in the identification of one cDNA clone, 38, that hybridized with both olignucleotides. This clone was purified and the insert cDNA was sequenced. Both of the determined amino acid sequences were encoded by clone 38 (see below), indicating that this clone was derived from authentic $\alpha^E$ mRNA. The entire 38 insert (0.8) was used to rescreen the library to identify clones that extended further in the 3' direction. Probes derived from the 3' ends of these and of subsequently identified cDNA clones were in turn used to successively rescreen the library. All clones used to produce the composite sequence were shown to detect transcripts of the same size in Northern blot analysis of TGF-β1 treated iIEL RNA. After five rounds of screening, a composite sequence was determined as the $\alpha^E$ coding sequence from cDNA clones 38, 1-39A, 2-54, and 3-15 (FIG. 1).

Extraneous sequences on the ends of the individual clones (broken lines) and sequences determined from insert ends or from deletion clones (horizontal arrows) also are illustrated in FIG. 1. In regions where the nucleotide sequence encoding $\alpha^E$ differed between clones, short stretches of other cDNA clones were used to establish a consensus. Two of these changes did not result in a frameshift in the open reading frame and may stem from genuine polymorphisms amongst alleles of $\alpha^E$. Alternatively, differences may represent artifactual point mutations in the cDNA clones generated during synthesis of the cDNA library or in its subsequent propagation. Specifically, at nucleotide 1205, cytosine, was replaced by adenosine in about one-third of the clones, resulting in a change in amino acid 342 from aspartic acid (D) to glutamic acid (E). At nucleotide 2193, cytosine was deleted in approximately one-sixth of the clones, resulting in a frameshift. At nucleotide 3247, guanosine was replaced by cytosine in about one-fifth of the clones, resulting in a change in amino acid 1023 from cysteine (C) to serine (S).

$\alpha^E$ Sequence Analysis:

A total of 3.9 kb of composite cDNA sequence was determined, which contained a 3.5 kb open reading frame (see Sequence I.D. Nos. 1 and 2). The 125 bp 5' untranslated region ended with a sequence characteristic of a translation initiation site (Hogervorst, F. et al., (1991) Eur. J. Biochem, 199, 425–433) and a methionine codon. (Sequence I.D. No. 1). This presumed initiation codon was the first residue in a stretch of 18 hydrophobic amino acids that was inferred to encode a signal sequence. This sequence ended in accordance with the (−3, −1) rule of von Heijne (von Heijne, G. (1986) Nucleic Acids Res. 14, 4683–4690), suggesting a likely site for cleavage by signal peptidase. The next 20 deduced amino acids were identical to those determined from peptide sequencing of the 25 kDa fragment. From amino acids 161–170 (Sequence I.D. No. 1), a deduced sequence identical to the determined peptide sequence from the 150 kDa fragment was found, confirming the smaller fragment to be N-terminal. Just prior to the second (150 kDa) peptide site were a pair of basic residues (RR). Similar motifs are found in several other integrin α subunits in which the cleavage site is preceded by two basic residues (Tamura, R. N. et al., (1990) J. Cell Biol. 111, 1593–1604; Teixido, J. et al., (1992) J. Biol. Chem. 267, 1786–1791; Takada, Y. et al., (1991) J. Cell. Biol. 115, 257–266; Argraves, W. et al., (1987) J. Cell. Biol. 105, 1183–1190; Song, W. K. et al., (1992) J. Cell. Biol. 117, 643–657; Bossy B. et al., (1991) EMBO J. 10, 2375–2385; Suzuki, S. et al., (1987) J. Biol. Chem. 262, 14080–14085; Poncz, M. et al., (1987) J. Biol. Chem. 262, 8476–8482), and may be the recognition site of an eukaryotic subtilisin-like protease (Barr, P. J. (1991) Cell 66, 1–3). A single potential N-glycan acceptor site was present in the first 159 residues which comprised the smaller fragment.

The deduced N terminus of the larger, 150 kDa, fragment was characterized by a highly charged sequence (Sequence I.D. No. 1, amino acids 161–180). Following the first two amino acids of this fragment (AL), 16 out of the following 18 amino acids were acidic and the remaining two were basic. Within the 150 kDa fragment deduced amino acid sequence, nine potential N-linked glycosylation sites were found, making a total of ten in the entire $\alpha^E$ sequence. A region of 23 hydrophobic amino acids (amino acids 1107–1129, Sequence I.D. No. 1) was predicted to encode a transmembrane region, followed by a cytoplasmic tail of 32 residues and a stop codon. Thus, the composite $\alpha^E$ cDNA predicted a typical type I transmembrane protein that was post-translationally cleaved towards the N terminus. The 270 bp of the predicted 3' untranslated sequence included a consensus polyadenylation signal (Sequence I.D. No. 1, aataaa) and a poly(A) tail.

The deduced amino acid sequence predicted a small fragment with a size of 20 kDa, allowing 2.5 kDa for its single potential N-linked glycosylation site. This value approximated the observed migration in SDS-PAGE of the smaller $\alpha^E$ subunit (25 kDa). With nine N-linked glycosylation sites, the predicted molecular mass for the larger fragment was 133 kDa, somewhat smaller that the estimate from SDS-PAGE of 150 kDa. This discrepancy between predicted molecular mass and migration in SDS-PAGE is similar to that observed for other integrin a subunits (Tamura, R. N. et al., (1990) J. Cell. Biol. 111, 1593–1604; Argraves, W. et al., (1987) J. Cell. Biol. 105, 1183–1190; Ignatius, M. J. et al., (1990) J. Cell. Biol. 111, 709–720)% The predicted pI of this larger subunit (5.2) may account for the difference in predicted and determined molecular weights as some negatively charged proteins migrate more slowly in SDS-PAGE than predicted from deduced molecular mass (Georges, E. et al., (1987) Eur. J. Biochem. 165, 281–287; Matagne, A. et al., (1991) Biochem. J. 280, 553–556).

Comparison of $\alpha^E$ With Other Integrin $\alpha$ Subunits:

The deduced amino acid sequence of $\alpha^E$ was manually aligned with that of other integrin $\alpha$ chains. The locations of cysteine and proline residues are often important in secondary structure of proteins, and were used as a primary basis for alignment, as were regions where blocks of amino acids showed strong homology with other integrin $\alpha$ subunits. In regions where homology was not readily apparent, gaps were arbitrarily introduced in the sequences in order to maximize alignment.

Comparison of the deduced $\alpha^E$ amino acid sequence (Sequence I.D. No. 2) with that of other integrin $\alpha$ subunits revealed the presence of many conserved features. Fourteen out of a total of 25 cysteine residues were conserved between $\alpha^E$ and other $\alpha$ chains. Immediately following the highly charged regions, a region of 193 amino acids homologous to typical I domains was present (Sequence I.D. No. 2, amino acids 182–373). Like other integrin $\alpha$ subunits, the $\alpha^E$ cDNA encoded seven repeated regions, the last three of which were potential divalent cation binding sites, resembling the EF-hand loop motif, with a consensus sequence corresponding to DXXXDXXD (SEQ ID NO:27) (Tuckwell, D. S. et al., (1992) Biochem J. 285, 325–331). The probable intracytoplasmic region contained the highly conserved GFFKR (SEQ ID NO:31) sequence (Sequence I.D. No. 1), which is present in every sequenced integrin $\alpha$ chain except the Drosophila PS2 $\alpha$ chain (GFFNR) (SEQ ID NO:28) (Brown, N. H. et al., (1989) Cell 59, 185–195), the chicken $\alpha^E$ chain (GFFDR) (SEQ ID NO:29) (Bossy, B. et al., (1991) EMBO J. 10, 2375–2385), and the hamster $\alpha^{3B}$ chain (DFFKP) (SEQ ID NO:30) (Tamura, R. N. et al., (1991) Proc. Natl. Acad. Sci. U.S.A. 88, 10183–10187).

Immediately preceding the presumed I domain was a stretch of 55 amino acids which did not align with other known $\alpha$ chains (Sequence I.D. No. 2, amino acids 127–181). For descriptive purposes, this region will be referred to as the 'extra' or X domain. Interestingly, the highly charged region described above (see $\alpha^E$ sequence analysis) and the unusually located cleavage site are within this X domain.

A homology tree was generated with the deduced amino acid sequence of $\alpha^E$ as compared to those of other integrin $\alpha$ subunits, using the computer program PILEUP. The program was executed both with complete sequences, as well as the sequences from with all I domains, and the X domain of $\alpha^E$ were removed. This was done to facilitate computer alignment of I domain containing integrin a subunits with those that lack this region. In each case, the overall shape of the homology tree generated was similar, although the branch point of $\alpha^E$ was slightly more closely related to the $\beta_2$ associated $\alpha$ chains ($\alpha^L$, $\alpha^M$, $\alpha^X$) than the $\beta_1$ associated $\alpha$ chains ($\alpha^1$ and $\alpha^2$) (FIGS. 2 and 3).

Figure 4:
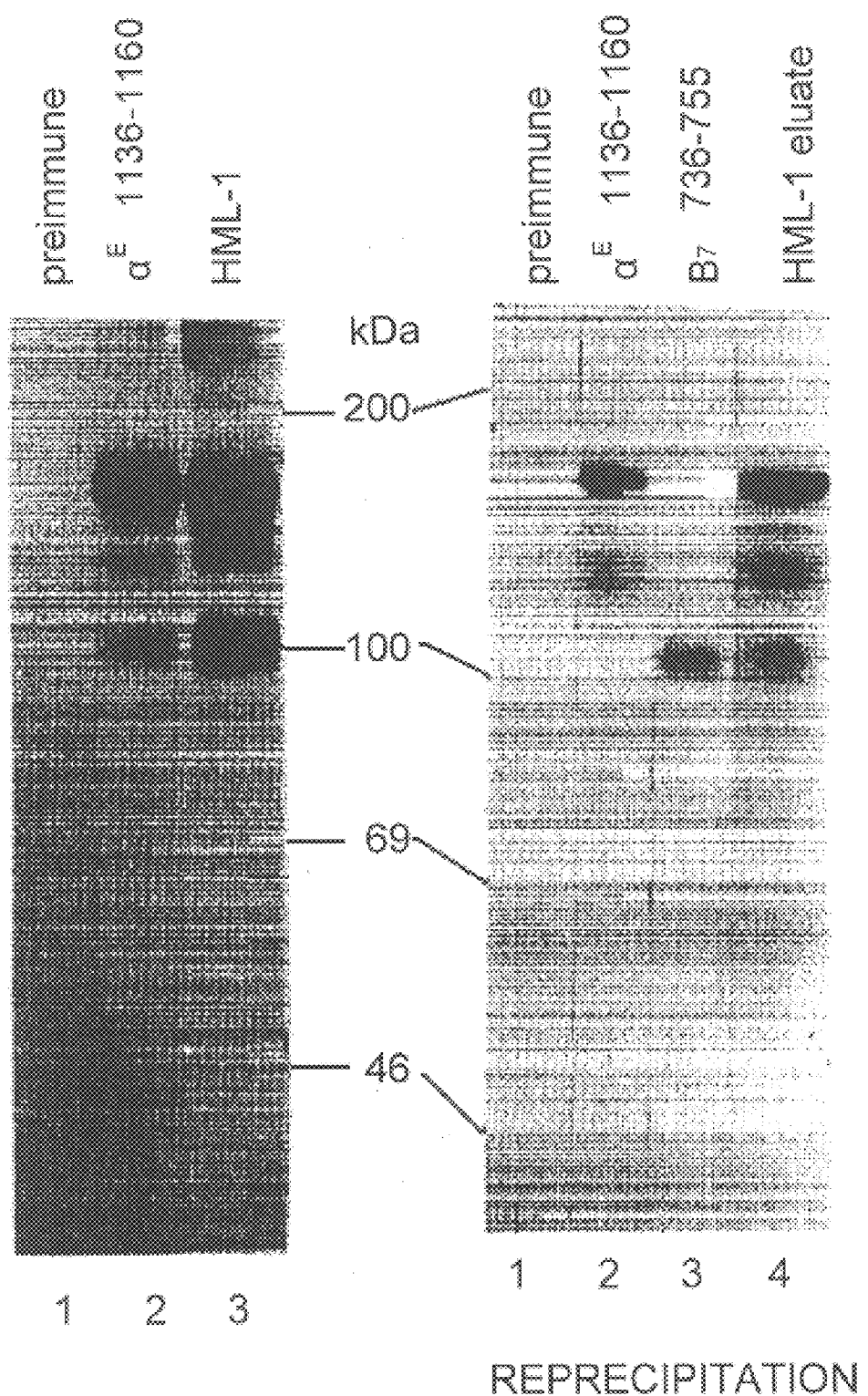
FIG. 4 illustrates the immunoprecipitation of the $\alpha^E$ subunit isolated from the HML-1 antigen with antiserum generated to the C-terminal peptide deduced from the $\alpha^E$ cDNA.

Confirmation that the Cloned cDNA Encodes $\alpha^E$:

A rabbit polyclonal antiserum was generated to a synthetic peptide corresponding to residues 11370–1161 of the deduced $\alpha^E$ amino acid sequence. This anti-$\alpha^E$ C-terminal peptide antiserum was used to immunoprecipitate polypeptides from a lysate of $^{125}$I-labelled cultured IEL. When this immunoprecipitate was resolved by SDS-PAGE under non-reducing conditions, a complex of polypeptides was observed, indistinguishable from that immunoprecipitated by the HML-1 mAb. This included the 175 kDa $\alpha^E$ subunit, the 105 kDa $\beta_7$ subunit, and two less well visualized intermediate sized polypeptides of 155 and 135 kDa (FIG. 4, lanes 2 and 3).

Next, the HML-1 complex was isolated by immunoprecipitation with the HML-1 mAb followed by elution of the component chains with SDS and heat. Equal aliquots of this immunoprecipitated and chain separated HML-1 complex were then reprecipitated with the HML-1 mAb, the anti-$\alpha^E$ C-terminal peptide antiserum, or an anti-$\beta_7$ C-terminal peptide antiserum (Parker, C. M. et al., (1992) Proc. Natl. Acad. Sci. U.S.A. 89, 1924–1928) and resolved by SDS-PAGE under non-reducing conditions. The anti-$\beta_7$ antiserum reprecipitated the 105 kDa $\beta_7$ polypeptide, but not the other species (FIG. 4, lane 6). The anti-$\alpha^E$ antiserum reprecipitated the $\alpha^E$ 175 kDa polypeptide as well as the 155 and 135 kDa species, but not the 105 kDa $\beta_7$ polypeptide (FIG. 4, lane 5). This indicated that the $\alpha^E$-antiserum recognized a polypeptide that was not only similar in size to, but also immunochemically cross-reactive with the polypeptides of 175, 155 and 135 kDa, recognized by the HML-1 mAb. Since the anti-$\alpha^E$ antiserum was generated to a deduced C-terminal amino-acid sequence that was distinct from the determined N-terminal amino acid sequences used to isolate the cDNA, these experiments offer independent evidence that the cDNA isolated encodes the same $\alpha^E$ subunit recognized by the HML-1 antibody. The reprecipitation experiment also offers clues to the identities of the 155 and 135 kDa species. Either these two additional polypeptides reassociated with the 175 kDa species after boiling in SDS, or, more likely, they directly interacted with the anti-$\alpha^E$ C-terminal peptide antiserum. Thus, these may be alternate structural forms of $\alpha^E$. Alternative RNA splicing (Tamura, R. N. et al., (1991) Proc. Natl. Acad. Sci. U.S.A. 88, 10183–10187; Tamura, R. N. et al., (1990) J. Cell. Biol. 111, 1593–1604; Hogervorst, F. et al., (1991) Eur. J. Biochem. 199, 425–433; Bray, P. F. et al., (1990) J. Biol. Chem. 265, 9587–9590; Zinrim, A. B. et al., (1990) J. Biol. Chem. 265, 8590–8595), alternative proteolytic processing (Calvete, J. J. et al., (1990) Febs Letters 272, 37–40; Loftus, J. C. et al., (1988) J. Biol. Chem. 263, 11025–11028), differential glycosylation (Sonnenberg, A. et al., (1990) J. Cell. Sci. 96, 207–217; Kim, L. T. et al., (1992) J. Cell. Sci. 103, 743–753; Hotchin, N. A. et al., (1992) J. Biol. Chem. 267, 14852–14858; Bednarczyk, J. L. et al., (1992) Clin. Exp. Metastasis 10, 281–290) and alternative tertiary structure of the same polypeptide backbone (Teixido, J. et al., (1992) J. Biol. Chem. 267, 1786–1791; Rubio, M. et al., (1992) Eur. J. Immunol. 22, 1099–1102) have all been reported to occur in other integrin α subunits, resulting in multiple cell-surface forms, and may account for this observation.

Figures 5A, 5B, 5C:
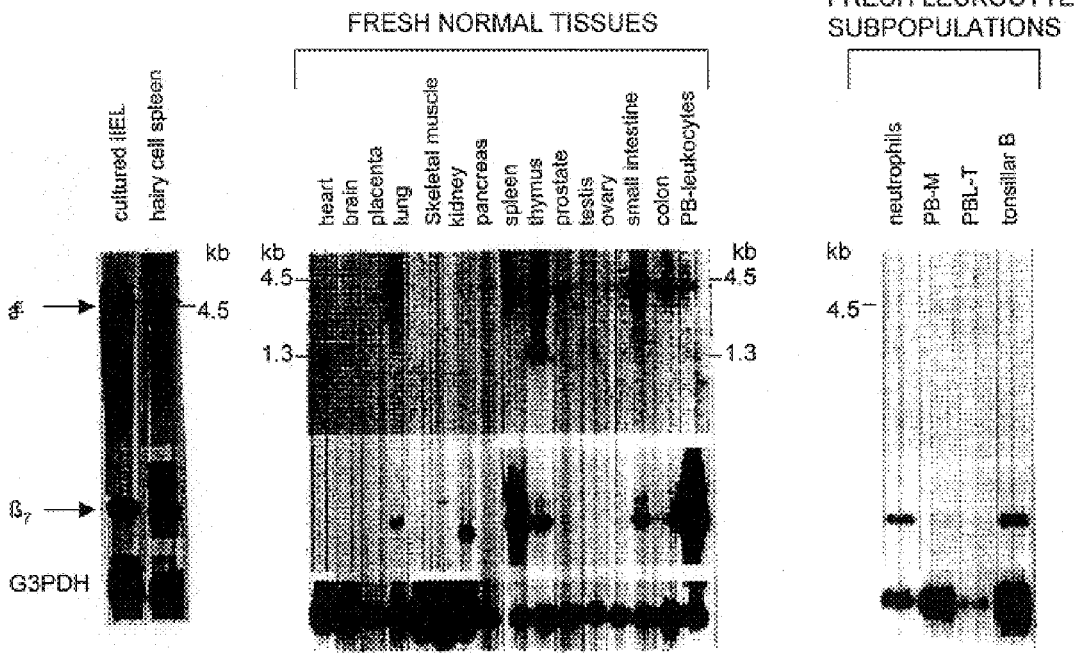
FIG. 5 illustrates the Northern blot analysis to determine the tissue distribution of $\alpha^E$ and $\beta_7$ mRNA.

Distribution of $\alpha^E$ mRNA Transcripts:

An $\alpha^E$ cDNA probe which spanned 1.2 kb of the coding sequence was used to analyze the distribution of $\alpha^E$ mRNA in normal tissues and in in vitro cultured lines. Freshly isolated human iIEL serve as a model of fresh iIEL in their surface expression of adhesion molecules (Cepek, K. L. et al., (1993) J. Immunol. 150, 3459–3470). Northern blot analysis of RNA from a TGF-β1 treated iIEL line indicated a single species of 4.5 kb that hybridized strongly with the $\alpha^E$ cDNA probe (FIG. 5A, seen as a broad smear in this exposure). As expected, the $\alpha^E$ species was also readily detected in RNA from the malignant hairy cell leukemia infiltrated spleen used to isolate protein for N-terminal amino acid sequencing. Moderate to low levels of the $\alpha^E$ mRNA were also detected in poly (A) enriched RNA from a range of normal human tissues (FIG. 5B) including lung, pancreas, spleen, thymus, prostate, testis, ovary, small intestine, colon, and peripheral blood leukocytes. To determine which leukocytes transcribe $\alpha^E$ mRNA, freshly isolated leukocytes were fractionated into their component sub-populations and analyzed by Northern analysis. Barely detectable levels of the $\alpha^E$ mRNA were found in poly (A) RNA from peripheral blood monocytes and T cells, as well as from tonsillar B cells, but not from neutrophils (FIG. 5C). Note that the tissue samples (FIG. 5B) contained 2–4 fold more RNA than did the cultured iIEL sample (FIG. 5A). Yet the al mRNA in cultured iIEL was much more strongly detected than in any of the normal tissues, indicating that $\alpha^E$ mRNA levels in these tissues were markedly lower than in iIEL. The $\alpha^E$ species was not detected in RNA from other tissues, including heart, brain, placenta, liver, skeletal muscle and kidney.

Figure 5D:
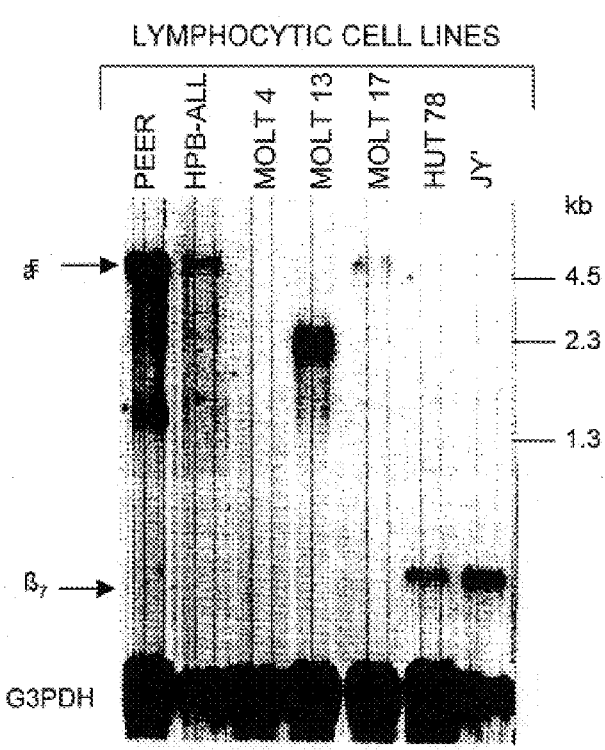
Figure 5E:
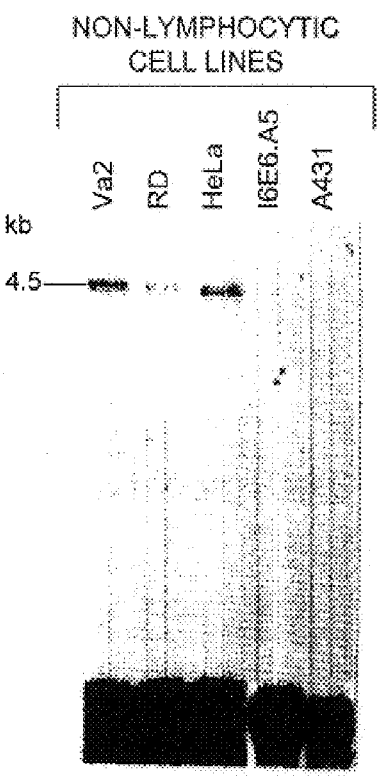

Analysis of tumor and transformed cell lines also was performed. In a panel of T cell tumors both γδ T cell receptor bearing cells (PEER and MOLT 13) and αβ T cell receptor bearing cells (HPB-ALL and MOLT 17) showed the $\alpha^E$ 4.5 kb mRNA. This transcript was not detected in other T cell tumors, including MOLT 4, HUT 78, nor in JY' (an Epstein-Barr virus-transformed B cell line selected for high surface expression of the β7 protein)(FIG. 5D). Amongst non-lymphocytic transformed or tumor cell lines, the 4.5 kb $\alpha^E$ mRNA species also was present in VA2 (fibroblast line), RD (rhabdomyosarcoma line), HeLa (cervical carcinoma line, epithelial like), and barely detected in 16E6. A5 but not in A431 (epithelial cell lines) (FIG. 5E).

Interestingly, in RNA from MOLT 13, 2.3 kb and 1.3 kb transcripts were detected, which hybridized more strongly with $\alpha^E$ cDNA than did the faintly visualized 4.5 kb $\alpha^E$ transcript (FIG. 5D). Both the 2.3 kb and 1.3 kb species also were detected in PEER, HPB-ALL and MOLT 17 T cell leukemia lines. These transcripts were apparent only upon hybridization with $\alpha^E$ cDNA, and not with $\beta^E$ cDNA or the positive control cDNA, suggesting that they were not due to non-specific binding of probe to the filter, but instead may represent cross-hybridization. The 2.3 kb transcript was detected only in RNA from tumor cell lines, but the 1.3 kb species was detected also in thymus and testis (FIG. 5B). Since integrin α subunit coding sequences are usually >3.3 kb, it seems unlikely that these transcripts represent alternatively spliced forms of $\alpha^E$ encoding a traditional integrin structure. These smaller species may be due to coincidental hybridization of a portion of the $\alpha^E$ cDNA probe to an unrelated transcript.

These same Northern blots were probed with a cDNA spanning the full length coding sequence of β7 in order to correlate the potential co-expression of β7 with $\alpha^E$. The β7 probe detected a 3 kb mRNA that hybridized abundantly with RNA derived from cultured iIEL and hairy cell spleen (FIG. 5A). Multiple tissues and cell lines which showed the presence of the 4.5 kb $\alpha^E$ transcript also showed the 3 kb β7 transcript, including lung, spleen, thymus, prostate, ovary, small intestine, colon, and peripheral blood leukocytes (FIG. 5B), fresh peripheral blood monocytes and T cells, tonsillar B cells (FIG. 5C), PEER, and also in MOLT 13 and MOLT 17 at barely detectable levels (FIG. 5D). This suggested that often the two transcripts were expressed coordinately. Many cells which transcribed both $\alpha^E$ and β7 also expressed the cell surface heterodimer as detected by immunostaining with anti-$\alpha^E$β7 mAbs of cultured iIEL (Cepek, K. L. et al., (1993) J. Immunol. 150, 3459–3470), hairy cell spleen (Moller, P. et al., (1990) Amer. J. Path. 136, 509–512; Visser, L. et al., (1989) Blood 74, 320–325), <2% of fresh peripheral blood lymphocytes (Cerf-Bensussan, N. et al., (1987) Eur. J. Immunol. 17, 1279–1285), tonsil, PEER, MOLT 13, and HPB-ALL$^b$. As expected, RNA from some sources showed the presence of the 3.0 kb β7 transcript in the absence of detectable $\alpha^E$, including fresh peripheral blood neutrophils (FIG. 5C), HUT 78 and JY' (FIG. 5D). Consistent with these findings, the β7 protein is known to be expressed in association with $\alpha^4$ and not with $\alpha^E$, on the surface of JY' cells (Chan, B. M. et al., (1992) J. Biol. Chem. 267, 8366–8370). Surprisingly, $\alpha^E$ transcripts were detected in the absence of detectable levels of β7 in RNA samples derived form pancreas and testis (FIG. 5B), HPB-ALL (FIG. 5D), and Va2, RD and HeLa and 16E6. A5 (FIG. 5E). In some tissues, the β7 DNA probe hybridized with mRNA species different in size from the primary 3 kb message including a 4.2 kb species in hairy cell spleen (FIG. 5A), skeletal muscle, normal spleen, thymus, small intestine, peripheral blood leukocytes (FIG. 5B), and tonsillar B cells (FIG. 5C); a 2.4 kb species in heart, liver, and kidney (FIG. 5B); and a 7 kb species in skeletal muscle. Although alternatively spliced forms of β7 have been reported (Erle, D. J. et al., (1991) J. Biol. Chem. 266, 11009–11016; Yuan Q. et al., (1992) J. Biol. Chem. 267, 7352–7358), the nature of the secondary β7 species reported here have not been evaluated.

Discussion:

The cDNA encoding a novel integrin α chain, $\alpha^E$, was cloned and sequenced revealing a type I transmembrane protein. Several lines of evidence indicated that the deduced amino acid sequence of the cDNA described here encodes the 175 kDa α subunit of the HML-1 antigen. Both peptide sequences determined from purification of the α subunit protein were encoded by the determined nucleotide sequence of the cloned gene. In addition, the $\alpha^E$ C-terminal peptide antiserum immunoprecipitated the same species as did the HML-1 antibody. Further, various biochemical features including a proteolytic cleavage site and the presence of N-linked glycosylation were consistent with known features of the HML-1 α chain.

Like other integrin α subunits, the deduced amino acid sequence of $\alpha^E$ contained seven repeated domains (the last three of which included potential divalent cation binding sites), an I domain, a pattern of conserved cysteine residues at positions similar to those in other integrin α subunits, and a GFFKR amino acid motif in the cytoplasmic domain. The $\alpha^E$ amino acid sequence was most closely related in overall structural features to the other I domain containing integrins since it contained a typical I domain, had three cation binding site consensus motifs, and lacked a membrane proximal cleavage site. In addition, in homology analysis, the $\alpha^E$ amino acid sequence was more homologous to the I domain containing α chains even in regions outside the I domain. However, $\alpha^E$ was a relatively distant member of the I domain containing group. This implies either that $\alpha^E$ diverged early from any potential I domain/integrin ancestral gene, or that this gene has undergone an accelerated rate of mutation.

While resembling other integrin α subunits in overall amino acid sequence, one region within $\alpha^E$ was unique. This region of 55 amino acids located just N-terminal to the I domain, did not bear homology to other integrin α chains. The proteolytic cleavage site of the $\alpha^E$ polypeptide was located between amino acids 160 and 161 in this extra or X domain. The $\alpha^E$ X domain thus accounted for both the unexpected cleavage of an I domain-containing integrin, as well as the unusual site of cleavage. Immediately following the cleavage site within the X domain was a stretch of 18 consecutive charged residues that comprised the N-terminal portion of the 150 kDa $\alpha^E$ fragment. This negatively charged stretch of amino acids is likely to be either solvent exposed or complexed to a moiety of the opposite charge. The charged stretch of $\alpha^E$ may be necessary to make the region accessible to the enzyme responsible for cleavage. Such a unique charged sequence seems likely to play an important role in both the structure and function of $\alpha^E$.

Analysis of the genomic structure of the classically cleaved integrin, $\alpha^{IIb}$ (Heidenreich, R. et al., (1990) Biochem 29, 1232–1244), has shown that the residues coding for its cleavage site lie within a single exon, not present in the traditional I domain containing integrins, $\alpha^M$ (Fleming, J. C. et al., (1993) J. Immunol. 150, 480–490) and $\alpha^X$ (Corbi, A. L. et al., (1990) J. Biol. Chem. 265, 2782–2788). This cleavage site-containing exon is thought to be the result of an insertion into an ancestral integrin gene. We speculate that in $\alpha^E$, the X domain containing the cleavage site may likewise correspond to an exon inserted just prior to the four exons that comprise the I domain in other integrins.

Previous studies utilizing immunohistochemistry have shown that the HML-1 protein is expressed in a highly restricted manner, primarily on mucosal lymphocytes (Cerf-Bensussan, N. et al., (1987) Eur. J. Immunol. 17, 1279–1285). In this study we confirmed the presence of high levels of $\alpha^E$ and $\beta_7$ mRNA in cultured iIEL. However, when poly(A) RNA from non-mucosal leukocytes was analyzed, barely detectable levels of $\alpha^E$ RA were found in fresh peripheral blood monocytes, T cells, and tonsillar B cells. As activated T and B lymphocytes and macrophages have been reported to express $\alpha^E\beta_7$ on the cell surface (Kruschwitz, M. et al., (1991) J. Clin. Path 44, 636–645; Pallesen, G. et al., (1990) Lancet 335, 537; Visser, L. et al., (1990) Brit. J. Haematol. 75, 359–365) it is possible that the $\alpha^E$ mRNA detected represents the small fraction amongst these predominantly resting cells that are activated. It is also possible that these low quantities are indicative of a basal level of transcription that may be upregulated in response to unknown stimuli, potentially conferring adhesive properties to these leukocytes mediated by $\alpha^E\beta_7$. When poly(A) RNA from a panel of tissues was analyzed, both $\alpha^E$ and $\beta_7$ mRNA also were detected in tissues known to have IEL, such as lung, small intestine and colon, and in lymphoid tissues, such as thymus and spleen. $\alpha^E$ and $\beta_7$ mRNA also were present at low levels in non-lymphoid tissues such as prostate and ovary, and $\alpha^E$ was observed in the absence of detectable $\beta_7$ in pancreas and testis. It is not known whether the $\alpha^E$ mRNA is present in tissue parenchymal cells, or is expressed in tissue resident leukocytes. Overall, the distribution of high levels of $\alpha^E$ mRNA supports the immunohistochemistry data in suggesting that cell-surface $\alpha^E\beta_7$ expression occurs predominantly on mucosal lymphocytes such as IEL and lamina propria lymphocytes in vivo. This restricted distribution implies that $\alpha^E\beta_7$ is important in localization of lymphocytes to mucosal tissues and/or a site-specific lymphocyte function.

Identification of the $\alpha^E\beta_7$ integrin and the genes that encode it make it possible to identify individuals with $\alpha^E$ or $\beta_7$ deficiency or produce targeted gene knock-out mice. The phenotype of these individuals may serve to illuminate additional functions of the $\alpha^E\beta_7$ molecule in vivo.

Example 2

An Adhesion Assay for Selecting Functionally Equivalent Peptide Analogs

The adhesion assay described herein is based upon the assay described by Cepek, K., et al., in J. Immunol. 150(8) :3459–3470 (1993), the entire contents of which are incorporated herein by reference.

The 16E6. A5 cell line was derived by immortalization of the 76N normal epithelial cell line through transfection of the E6 and E7 genes of human papilloma virus (by V. Band, Tufts University, publically available). Monolayers of these adherent cells are grown in flat-bottomed 96-well Linbro tissue culture plates. $10^4$ adherent cells in 100 ul complete media are added per well and allowed to grow for 3 days until they reach confluence. Just before the addition of iIEL, these cells are washed with assay media. To label iIEL, 25 μg of 2',7'-bis-(2-carboxyethyl)-5 (and 6)-carboxyfluorescein (BCEFC-AM, Molecular Probes, Inc., Eugene, Oreg.) is diluted in 5 μl DMSO and added to a suspension of $5\times10^6$/ml IEL in complete Yssel's media. The cells are incubated at 37 degrees C. for 35 min then washed twice in assay media (phosphate buffered saline "PBS" or RPMI tissue culture media, available from GIBCO or Sigma Chemical Corp., St. Louis, Mo., containing 1 mM CaCl$_2$, 2 mM MgCl$_2$, and 10 mM HEPES). After washing, 50,000 labeled iIEL in 100 μl of assay media are added to the adherent cell monolayers. iIEL are allowed to settle onto adherent cell monolayers for 25 min or 40 min at 37 degrees C. Unbound cells are removed by flicking media from the plate. Bound cells are detected using a Fluorescence plate reader (IDEXX Co., Portland Md.). If antibody blocking is performed, the iIEL are preincubated with an appropriate concentration of antibody (e.g., a 1/250 dilution of ascites fluid or 10 ug/ml of purified mAb) for 5 in at 37 degrees C before addition to the adherent cell monolayers. At least four replicates were performed. The % cells bound is calculated by reading the fluorescence units obtained after unbound cells are washed off and dividing this number by the input fluorescence units obtained after adding 50,000 cells/well and multiplying by 100. Serial dilutions of labeled cells have shown that as few as 1000 cells can be detected in the linear range.

To screen a molecular library or other mixture for the presence of a functionally equivalent peptide analog, the iIEL are washed with HBSS (Hanks buffered saline solution, available from Gibco) and pre-equilibrated with HBSS containing serial dilutions of the library or other peptide-containing solution (over a broad concentration range (e.g. 1 ng/ml to 100 ug/ml) for selected times (e.g., 30 min, 1 hour, 2 hours, 6 hours) at 37 degree C before incubation with 16E6.A5 monolayers that have been washed with HBSS. Functionally equivalent peptide analogs are identified by their ability to inhibit the binding of cells to the monolayer of adherent cells.

It should be understood that the preceding is merely a detailed description of certain preferred embodiments. It therefore should be apparent to those skilled in the art that various modifications and equivalents can be made without departing from the spirit and scope of the invention.

A sequence listing is presented below and is followed by what is claimed:

What is claimed is:

1. A method for treating ulcerative colitis, the method comprising
administering to a subject in need of such treatment a therapeutically effective amount of an antibody that selectively binds to an $\alpha^E\beta_7$ integrin.

2. A method for treating ulcerative colitis, the method comprising
administering to a subject in need of such treatment a therapeutically effective amount of an antibody that selectively binds to an integrin $\alpha^E$ subunit.

3. A method for treating Crohn's disease, the method comprising administering to a subject in need of such treatment a therapeutically effective amount of an antibody that selectively binds to an $\alpha^E\beta_7$ integrin.

4. A method for treating Crohn's disease, the method comprising
administering to a subject in need of such treatment a therapeutically effective amount of an antibody that selectively binds to an integrin $\alpha^E$ subunit.

* * * * *